US011484223B2

(12) United States Patent
Kostic et al.

(10) Patent No.: US 11,484,223 B2
(45) Date of Patent: Nov. 1, 2022

(54) PERSON SUPPORT APPARATUSES WITH MOTION MONITORING

(71) Applicant: Stryker Corporation, Kalamazoo, MI (US)

(72) Inventors: Marko N. Kostic, Johnson City, TN (US); Jonathan Mark Greenbank, Plainwell, MI (US)

(73) Assignee: Stryker Corporation, Kalamazoo, MI (US)

( * ) Notice: Subject to any disclaimer, the term of this patent is extended or adjusted under 35 U.S.C. 154(b) by 248 days.

(21) Appl. No.: 16/441,225

(22) Filed: Jun. 14, 2019

(65) Prior Publication Data

US 2019/0290169 A1 Sep. 26, 2019

Related U.S. Application Data

(63) Continuation of application No. 14/873,734, filed on Oct. 2, 2015, now Pat. No. 10,357,185.

(Continued)

(51) Int. Cl.
*A61B 5/11* (2006.01)
*A61G 7/05* (2006.01)
(Continued)

(52) U.S. Cl.
CPC .......... *A61B 5/1115* (2013.01); *A61B 5/1036* (2013.01); *A61B 5/1116* (2013.01);
(Continued)

(58) Field of Classification Search
CPC .. A61G 7/0527; A61G 5/1036; A61G 5/1115; A61G 5/1116; A61G 5/1121;
(Continued)

(56) References Cited

U.S. PATENT DOCUMENTS 4,869,266 A * 9/1989 Taylor .................... A61M 1/00
600/587
4,934,468 A * 6/1990 Koerber, Sr. ........ G01G 19/445
128/897

(Continued)

FOREIGN PATENT DOCUMENTS

WO    WO-03079953 A2 * 10/2003    ......... A61G 7/05715

OTHER PUBLICATIONS

Stryker Operations Manual InTouch Critical Care Bed Model FL27, Version 2.5, Apr. 2012.

(Continued)

*Primary Examiner* — David R Hare
(74) *Attorney, Agent, or Firm* — Warner Norcross + Judd LLP

(57) ABSTRACT

A person support apparatus, such as a bed, cot, stretcher, or the like, includes an exit detection system that utilizes an occupant motion parameter to determine whether to issue an alert or not. The motion parameter may be based on the weight and motion of the occupant. Successive positions of the occupant are determined in order to calculate a velocity of the occupant. In some embodiments, the kinetic energy of the occupant is used to determine if an alert should be issued. Objects positioned on the person support apparatus may also be detected and tracked. Auto-zeroing of a built-in scale, as well as automatic recognition of the removal, movement, and/or addition of objects is also provided.

23 Claims, 11 Drawing Sheets

Related U.S. Application Data

(60) Provisional application No. 62/065,242, filed on Oct. 17, 2014.

(51) Int. Cl.
| | | |
|---|---|---|
| *A61B 5/00* | (2006.01) | |
| *A61B 5/103* | (2006.01) | |
| *G16H 40/63* | (2018.01) | |
| *G16H 40/20* | (2018.01) | |
| *G16H 50/30* | (2018.01) | |

(52) U.S. Cl.
CPC .......... *A61B 5/1121* (2013.01); *A61B 5/6892* (2013.01); *A61B 5/7275* (2013.01); *A61G 7/0507* (2013.01); *A61G 7/0527* (2016.11); *G16H 40/20* (2018.01); *A61B 2562/0252* (2013.01); *G16H 40/63* (2018.01); *G16H 50/30* (2018.01)

(58) Field of Classification Search
CPC .... A61G 5/6892; A61G 5/7275; G16H 40/20; G16H 40/63; A61B 2562/0252
See application file for complete search history.

(56) References Cited

U.S. PATENT DOCUMENTS

| | | | | | |
|---|---|---|---|---|---|
| 4,953,244 | A  * | 9/1990 | Koerber, Sr. | ........ | G01G 19/445 5/600 |
| 5,276,432 | A  * | 1/1994 | Travis | .................... | G08B 21/22 177/144 |
| 5,861,582 | A  * | 1/1999 | Flanagan | ................ | G01G 3/13 177/144 |
| 6,518,520 | B2 * | 2/2003 | Jones | .................. | G01G 19/445 177/144 |
| 7,472,439 | B2 * | 1/2009 | Lemire | ................. | A61G 7/005 177/144 |
| 7,610,637 | B2 * | 11/2009 | Menkedick | .............. | A61G 7/00 5/611 |
| 7,703,158 | B2 * | 4/2010 | Wilker, Jr. | ............. | A61G 7/015 5/616 |
| 7,962,981 | B2 * | 6/2011 | Lemire | ................... | B60T 7/085 5/616 |
| 10,045,715 | B2 * | 8/2018 | Hoffman | ................ | G01G 19/52 |
| 10,357,185 | B2 * | 7/2019 | Kostic | .................. | A61B 5/6892 |
| 10,898,400 | B2 * | 1/2021 | Kostic | .................. | A61G 7/0527 |
| 2011/0066383 | A1 * | 3/2011 | Jangle | ................ | G06K 9/00342 702/19 |
| 2012/0089419 | A1 * | 4/2012 | Huster | ................... | A61G 7/018 705/3 |
| 2013/0146371 | A1 * | 6/2013 | Shih | ..................... | G01G 19/445 177/144 |
| 2013/0247300 | A1 * | 9/2013 | Menke | ............... | A61G 13/1225 5/611 |
| 2014/0124273 | A1 * | 5/2014 | Receveur | ............ | A61G 7/0527 177/1 |
| 2014/0266733 | A1 * | 9/2014 | Hayes | .................. | A61B 5/0205 340/573.4 |
| 2016/0081592 | A1 * | 3/2016 | Ishikawa | .............. | A61B 5/1121 5/600 |
| 2017/0234723 | A1 * | 8/2017 | Charles | ................ | A61B 5/1036 5/600 |

OTHER PUBLICATIONS

Stryker Operations Manual InTouch Critical Care Bed Model FL27, Version 2.4, Jun. 2010.
CHG Hospital Beds "User Manual for Spirit One Beds".
Stryker Operations Manual, S3 MedSurg Bed with StayPut Frame, Model 3005, Mar. 2012.
Stryker Operations Manual MedSurg Bed, Model 3002 S3, Oct. 2010.
Stryker Medical Secure 3000 Bed Operations Manual.

* cited by examiner

PERSON SUPPORT APPARATUSES WITH MOTION MONITORING

CROSS-REFERENCE TO RELATED APPLICATIONS

This application claims priority to U.S. patent application Ser. No. 14/873,734 filed Oct. 2, 2015, by inventors Marko Kostic et al. and entitled PERSON SUPPORT APPARATUSES WITH MOTION MONITORING, which in turn claims priority to U.S. provisional patent application Ser. No. 62/065,242 filed Oct. 17, 2014 by inventors Marko Kostic et al. and entitled PERSON SUPPORT APPARATUSES WITH MOTION MONITORING, the complete disclosures of both of which are incorporated herein by reference.

BACKGROUND

The present disclosure relates to person support apparatuses, such as beds, cots, stretchers, operating tables, recliners, or the like. More specifically, the present disclosure relates to person support apparatuses that include sensors for monitoring the motion of an occupant of the person support apparatus.

Existing hospital beds and/or stretchers often include a bed exit system that is adapted to detect when a patient has exited the bed, or when a patient may be about to exit the bed. Typically, such beds include circuitry for providing an audio or visual alert when such an exit or pre-exit situation is detected. In many cases, the bed or stretchers include circuitry for transmitting a signal to a remote location, such as a nurses' station, so that the appropriate caregivers are notified of the exit, or pre-exit condition, and can respond appropriately.

SUMMARY

According to various embodiments, an improved person support apparatus is provided having a motion monitoring system that monitors and analyzes the motion of an occupant and/or objects located on the person support apparatus in order to provide more useful information to caregivers. In some embodiments, the motion is monitored and analyzed to provide improved alerting regarding an occupant's intention to exit the bed, including advanced notification of such an exit. In other embodiments, the motion is monitored and analyzed in order to provide a reduction in false alarms regarding an occupant's intention to exit the person support apparatus. In still other embodiments, the motion is monitored and analyzed for purposes other than predicting or detecting occupant's departure, such as, but not limited to, determining the occupant's overall level of movement in order to assist in the prevention or mitigation of decubitus ulcers.

According to one embodiment of the disclosure, a person support apparatus is provided that includes a support surface adapted to support thereon an occupant of the person support apparatus; a plurality of force sensors adapted to determine a weight of the occupant of the support surface; and an exit detection system. The exit detection system is adapted to issue an alert if the occupant of the person support apparatus is moving toward exiting the support surface. The exit detection system is further adapted to take into account the weight of the occupant in determining whether or not the occupant is moving toward exiting the support surface.

In another embodiment, the person support apparatus includes a user interface adapted to allow a user of the person support apparatus to select from a plurality of zones, and the exit detection system is further adapted to issue the alert if the occupant of the person support apparatus is moving toward exiting a selected one of the plurality of zones. The exit detection system taking into account the weight of the occupant in determining whether or not the occupant is moving toward exiting the selected one of the plurality of zones.

In another embodiment, the exit detection system is adapted to perform the following: use the weight of the occupant to calculate a first quantity that is directly proportional to a kinetic energy of the occupant; repetitively determine a motion parameter that is a function of the first quantity; compare the motion parameter to a first threshold; increment a motion parameter counter if the motion parameter exceeds a first threshold; compare the motion parameter counter to a second threshold; and issue the alert if the motion parameter counter exceeds the second threshold.

The exit detection system is further adapted, in at least one embodiment, to change the second threshold based upon any one or more of the following: a direction of movement of the occupant; an angular orientation of a pivotable head section of the support surface; and/or a position of a siderail.

According to another embodiment of the disclosure, a person support apparatus is provided that includes a support surface adapted to support thereon an occupant of the person support apparatus; a siderail positioned adjacent to the support surface, the siderail movable between a raised position and a lowered position; and an exit detection system. The exit detection system is adapted to issue an alert if the occupant of the person support apparatus moves in a manner that meets a set of criteria. The exit detection system is further adapted to change the set of criteria based upon whether or not the siderail is in the raised position or the lowered position.

In another aspect, the set of criteria includes both a speed of movement of the occupant and a direction of movement of the occupant. The exit detection system also changes the set of criteria based upon an angular orientation of the head section according to another embodiment.

In other embodiments, the exit detection system determines a motion parameter that is a function of an amount of kinetic energy of the occupant and compares the motion parameter to a threshold that is part of the set of criteria. The threshold is changeable based upon any one or more of the following: whether the siderail is raised or lowered, what direction the occupant is moving in, an initial position of the occupant on the support surface; and/or an angle of a head section of the support surface.

In still other embodiments, the exit detection system determines whether the occupant is sitting up or lying down. The exit detection system may further change the set of criteria based upon whether or not the occupant is sitting up or lying down.

The exit detection system, in at least one embodiment, includes a plurality of force sensors in communication with a controller. In at least one other embodiment, the plurality of force sensors are load cells coupled to a frame of the person support apparatus and positioned so as to provide support to the support surface.

The exit detection system calculates a center of gravity of the occupant and tracks movement of the center of gravity in an embodiment. Further, the exit detection system may calculate a velocity of the center of gravity and use the velocity to determine whether the occupant is moving in a manner that meets the set of criteria.

According to another embodiment of the disclosure, a person support apparatus is provided that includes a support surface and an exit detection system. The support surface is adapted to support thereon an occupant of the person support apparatus. The exit detection system is adapted to determine a kinetic energy of the occupant and to use the kinetic energy in deciding whether to issue an alert. The alert provides an indication that the occupant of the support surface may be about to exit the support surface.

In another embodiment, the exit detection system further includes force sensors adapted to determine a weight of the occupant and to use the weight when determining the kinetic energy of the occupant. The exit detection system may further be adapted to use outputs of the force sensors to determine a direction of movement of the occupant.

In at least one embodiment, the exit detection system comprises a controller adapted to calculate a motion parameter based on the kinetic energy of the occupant, to compare the motion parameter to a first threshold, to increment a motion parameter counter if the motion parameter exceeds the first threshold, to compare the motion parameter counter to a second threshold, and to issue the alert if the motion parameter counter exceeds the second threshold.

The second threshold may vary based upon any one or more of the following: the direction of movement of the occupant, a position of a siderail, an initial position of the occupant on the support surface; and/or an angle of a head section of the support surface.

In another embodiment, the person support apparatus further comprises: a right head siderail, a right foot siderail, a left head siderail, and a left foot siderail, and each of these siderails is movable between a raised position and a lowered position. Further, the exit detection system sets the second threshold to a first value when the motion parameter of the occupant is associated with movement toward either the right head siderail or the left head siderail, and sets the second threshold to a second value when the motion parameter of the occupant is associated with movement toward either the right foot siderail or the left foot siderail. The second threshold may have a third value when the motion parameter of the occupant is directed to a foot end of the support surface.

In another embodiment, the exit detection system calculates the kinetic energy of the occupant by determining a velocity of a center of gravity of the occupant.

According to another embodiment of the disclosure, a person support apparatus is provided that includes a frame, a deck, a plurality of force sensors, and a controller. The deck is supported on the frame and has a support surface adapted to support an object thereon. The plurality of force sensors are adapted to detect forces exerted onto the deck. The controller is in communication with the force sensors and is adapted to detect movement of the object on the support surface and to determine whether the object is an animate object or an inanimate object based upon the detected movement.

The controller may further be adapted to determine a weight of the object based upon the forces detected by the force sensors.

In at least one embodiment, the force sensors are coupled between the frame and a load frame so as to support the load frame on the frame. The load frame supports the deck.

In another embodiment, the controller is adapted to determine if a second object is subsequently placed on the support surface and to determine a weight of the second object without requiring the first object to be removed from the support surface. The controller may further be adapted to repetitively determine and record a location of the second object. Still further, the controller may be adapted to determine whether the second object is an animate object or an inanimate object based upon movement of the second object.

In another embodiment, the controller is adapted to re-determine a weight of the object after the second object is placed on the support surface without requiring the first object to be removed. The controller may also be adapted to monitor a velocity of the object, if the object is an animate object, and to issue an alert if a motion parameter based on the velocity of the animate object exceeds a threshold.

According to another embodiment of the disclosure, a person support apparatus is provided that includes a frame, a deck supported on the frame, a scale system, a memory, and a controller in communication with the scale system and memory. The deck includes a support surface adapted to support an object thereon. The scale system is adapted to detect a weight of the deck and any object positioned thereon. The memory has stored therein an estimated tare weight value for the scale system as determined by a manufacturer of the person support apparatus. And the controller uses an actual weight reading from the scale system as an actual tare weight value if the actual weight reading is within a threshold amount of the estimated tare weight value.

According to another embodiment, the controller uses the actual tare weight value when determining the weight of a person on the deck.

In another embodiment, the controller automatically uses the actual weight reading from the scale system as the actual tare weight value without requiring a user to manipulate a control on the person support apparatus instructing the scale system to take the actual weight reading.

The memory may further include a second estimated tare weight value, wherein the controller is adapted to use the actual weight reading from the scale system as the actual tare weight value if the actual weight reading is within the threshold amount of the second estimated tare weight value. The second estimated tare weight value is based upon a weight of one or more of a mattress, pillow, bedding, or equipment.

The controller, in at least one embodiment, is further adapted to determine whether the object is an animate object or an inanimate object based upon any changes in a location of the object. The controller may further be adapted to determine if a second object is subsequently placed on the support surface and to determine the weight of the second object without requiring the object to be removed from the support surface. Still further, the controller automatically adjusts the actual tare weight value by an amount substantially equal to the weight of the second object if the second object is an inanimate object, in at least one embodiment.

In at least one embodiment, the controller also determines the location of the second object. For example, in one embodiment, the controller examines the center of gravity of the second object before adjusting the actual tare weight to determine if the location of the second object corresponds to the expected location for that object (e.g. a mattress has a center of gravity near the center of the support surface, or a pillow has a center of gravity near a head end of the bed, etc.). If both the expected weight and location match, the actual tare weight is adjusted. If they do not both match, the controller does not adjust the actual tare weight.

According to still another embodiment, a person support apparatus is provided that includes a support surface, a plurality of force sensors, a control, and an exit detection system. The support surface is adapted to support thereon an occupant of the person support apparatus. The plurality of force sensors are adapted to detect downward forces exerted by the occupant onto the support surface. The control allows a user to select one of a plurality of zones defined with respect to the support surface. The exit detection system is adapted to determine if the occupant of the person support apparatus is likely to move outside of a selected one of the plurality of zones and to issue an alert indicating that the person is likely to move outside of the selected one of the plurality of zones. The exit detection system issues the alert prior to the occupant actually moving outside of the selected one of the zones.

In any of the embodiments disclosed herein, the person support apparatus may further include a base having a plurality of wheels; a frame that supports the support surface; a height adjustment mechanism coupled between the frame and the base that is adapted to change the height of the frame with respect to the base; and an articulating deck supported on the frame wherein the articulating deck has an upper surface that defines the support surface.

Before the various embodiments disclose herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
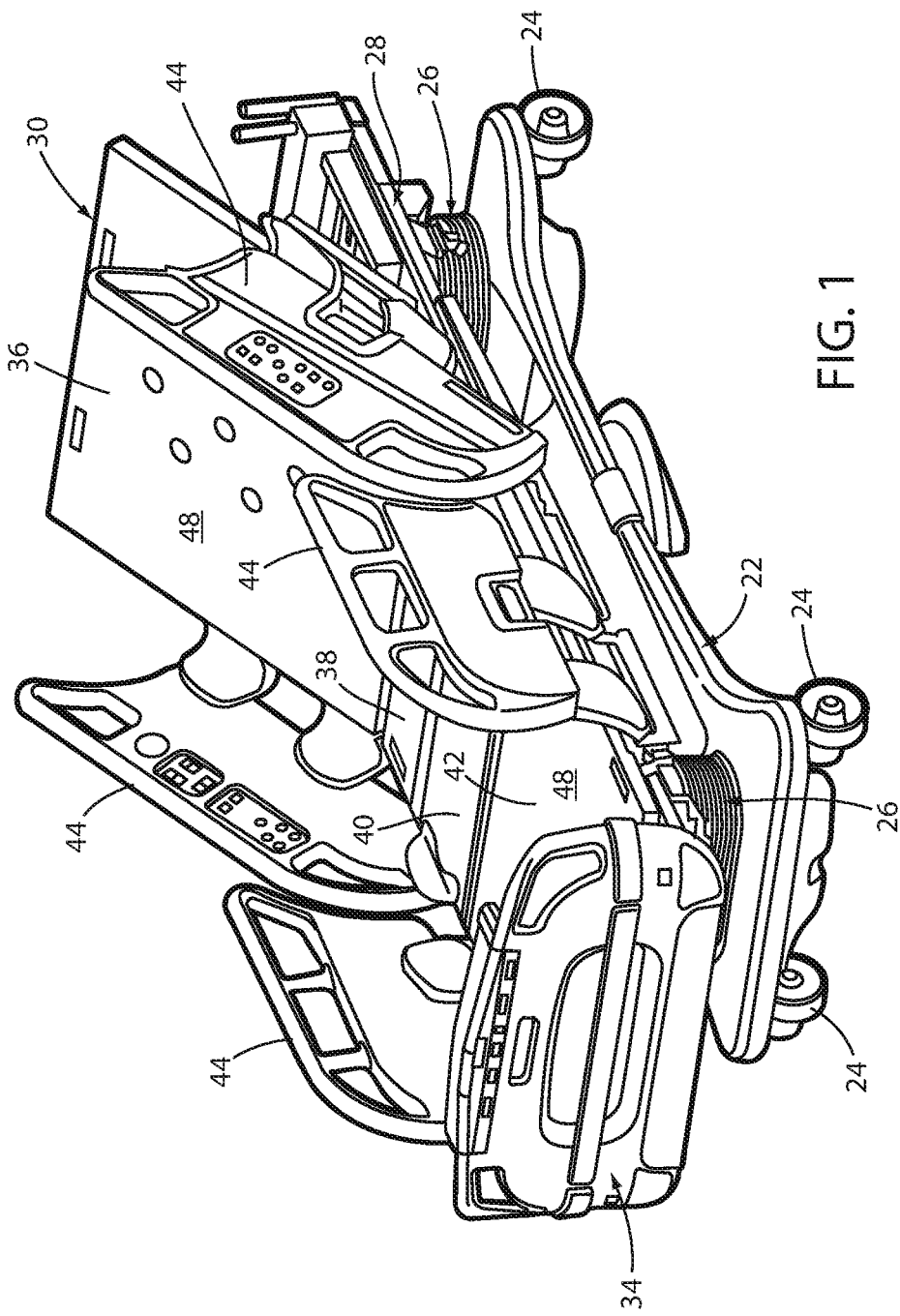
FIG. 1 is a perspective view of a person support apparatus according to one embodiment of the disclosure.

A person support apparatus 20 according to one embodiment of the disclosure is shown in FIG. 1. Although the particular form of person support apparatus 20 illustrated in FIG. 1 is a bed adapted for use in a hospital or other medical setting, it will be understood that person support apparatus 20 could, in different embodiments, be a cot, a stretcher, a gurney, a recliner, an operating table, a residential bed, or any other structure capable of supporting a person, whether stationary or mobile and/or whether medical or residential.

In general, person support apparatus 20 includes a base 22 having a plurality of wheels 24, elevation adjustment mechanisms 26 supported on the base, a frame or litter 28 supported on the elevation adjustment mechanisms, and a support deck 30 supported on the frame. Person support apparatus 20 further includes a headboard 32 and a footboard 34.

Base 22 includes a brake that is adapted to selectively lock and unlock wheels 24 so that, when unlocked, person support apparatus 20 may be wheeled to different locations. Elevation adjustment mechanisms 26 are adapted to raise and lower frame 28 with respect to base 22. Elevation adjustment mechanisms 26 may be hydraulic actuators, electric actuators, or any other suitable device for raising and lowering frame 28 with respect to base 22. In some embodiments, elevation adjustment mechanisms 26 are operable independently so that the orientation of frame 28 with respect to base 22 can also be adjusted.

Frame 28 provides a structure for supporting support deck 30, headboard 32, and footboard 34. Support deck 30 provides a support surface 48 on which a mattress (not shown), or other soft cushion is positionable so that a person may lie and/or sit thereon. Support deck 30 is made of a plurality of sections, some of which are pivotable about generally horizontal pivot axes. In the embodiment shown in FIG. 1, person support deck 30 includes a head section 36, a seat section 38, a thigh section 40, and a foot section 42. Head section 36, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 40 and foot section 42 may also be pivotable.

A plurality of siderails 44 (FIG. 1) may also be coupled to frame 28. If person support apparatus 20 is a bed, there may be four such siderails, one positioned at a left head end of frame 28, a second positioned at a left foot end of frame 28, a third positioned at a right head end of frame 28, and a fourth positioned at a right foot end of frame 28. If person support apparatus 20 is a stretcher or a cot, there may be fewer siderails. In other embodiments, there may be no siderails on person support apparatus 20. Regardless of the number of siderails, such siderails are movable between a raised position in which they block ingress and egress into and out of person support apparatus 20, and a lowered position in which they are not an obstacle to such ingress and egress.

The construction of any of base 22, elevation adjustment mechanisms 26, frame 28, support deck 30, headboard 32, footboard 34, and/or siderails 44 may take on any known or conventional design, such as, for example, that disclosed in commonly assigned, U.S. Pat. No. 7,690,059 issued to Lemire et al., and entitled HOSPITAL BED, the complete disclosure of which is incorporated herein by reference; or that disclosed in commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosure of which is also hereby incorporated herein by reference. The construction of any of base 22, elevation adjustment mechanisms 26, frame 28, support deck 30, headboard 32, footboard 34 and/or the siderails may also take on forms different from what is disclosed in the aforementioned patent and patent publication.

Figure 2:
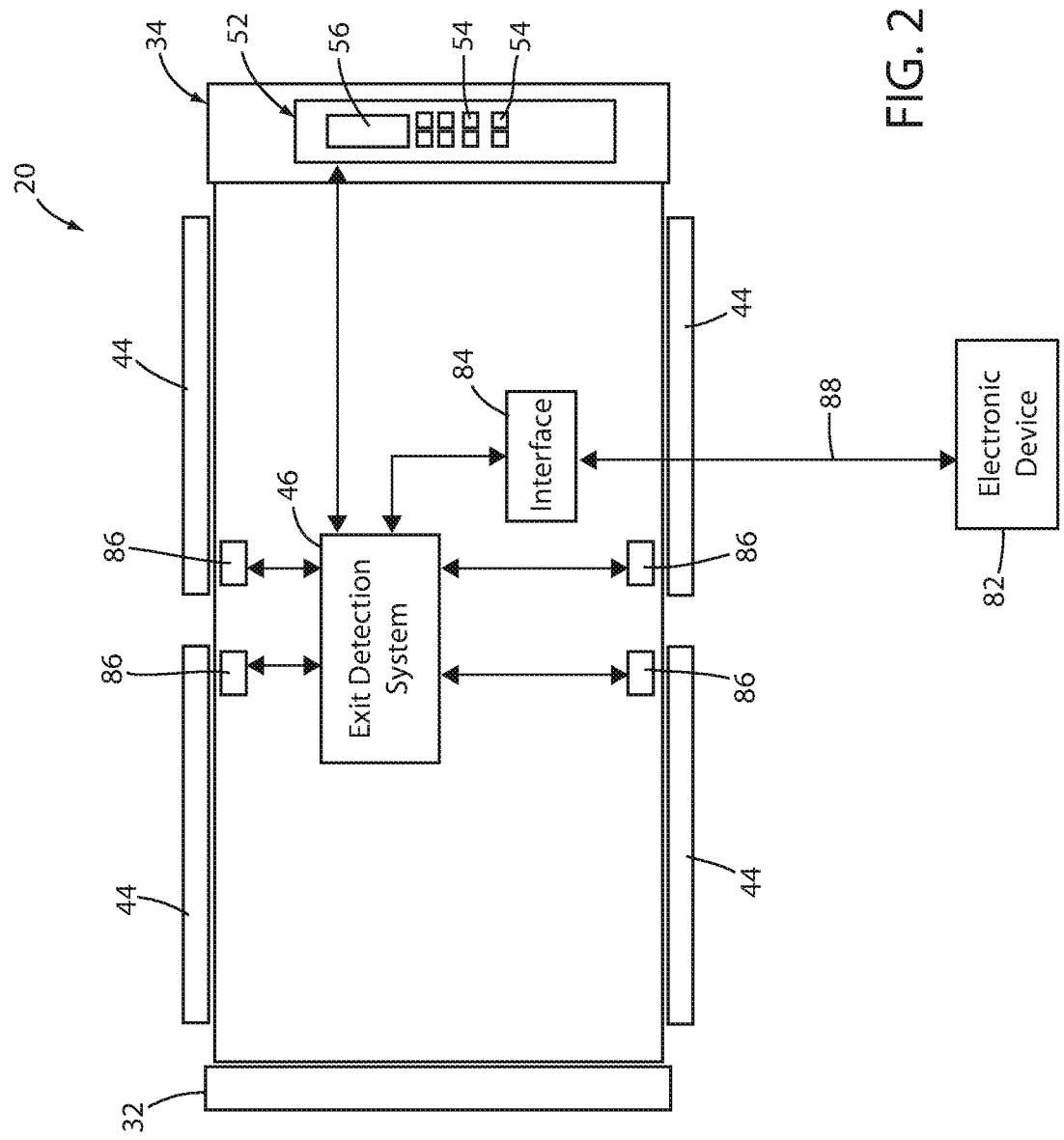
FIG. 2 is a diagram of the person support apparatus of FIG. 1 showing a first embodiment of an exit detection system that may be incorporated therein.

As shown more clearly in FIG. 2, person support apparatus 20 includes an exit detection system 46 that is adapted to determine when an occupant, such as, but not limited to, a patient, of person support apparatus 20 is likely to exit person support apparatus 20. More specifically, person support apparatus 20 is adapted to determine when an occupant is likely to leave prior to the occupant actually leaving, and to issue an alert and/or notification to appropriate personnel so that proper steps can be taken in response to the occupant's imminent departure in a more timely fashion. The particular structural details of exit detection system 46 can vary widely. In one embodiment, exit detection system 46 includes a pressure sensing array that is laid on top of, or integrated into, a mattress (not shown) positioned on top of support surface 48. Such a pressure sensing array is constructed, in at least one embodiment, in any of the manners disclosed in commonly assigned U.S. patent application Ser. No. 14/003,157 filed Oct. 14, 2013 by inventors Joshua Mix et al. and entitled SENSING SYSTEM FOR PATIENT SUPPORTS; or in any of the manners disclosed in commonly assigned U.S. patent application Ser. No. 14/019,089 filed Sep. 5, 2013 by inventor Geoffrey Taylor and entitled ADAPTIVE CUSHION METHOD AND APPARATUS FOR MINIMIZING FORCE CONCENTRATIONS ON A HUMAN BODY, the complete disclosure of both of which are incorporated herein by reference.

In other embodiments, exit detection system 46 is constructed to include one or more infrared sensors that detect and process thermal images of the occupant of person support apparatus 20 in order to determine the position and movement of the occupant. For example, in at least one embodiment, exit detection system 46 is constructed in any of the manners disclosed in commonly assigned U.S. patent application Ser. No. 61/989,243 filed May 6, 2014 by inventors Marko Kostic et al. and entitled PERSON SUPPORT APPARATUS WITH POSITION MONITORING, the complete disclosure of which is also incorporated herein by reference.

When exit detection system 46 is constructed to utilize any of the pressure sensing arrays or thermal imaging sensors disclosed in the three above-identified patent applications, exit detection system 46 processes the outputs from the pressure sensors and/or thermal image sensors to determine the movement and location of the occupant, and then determines from this movement and location information whether or not an impending exit of the occupant from person support apparatus 20 is likely. The determination of whether an impending exit is likely is carried out in any of the manners discussed below.

Figure 2A:
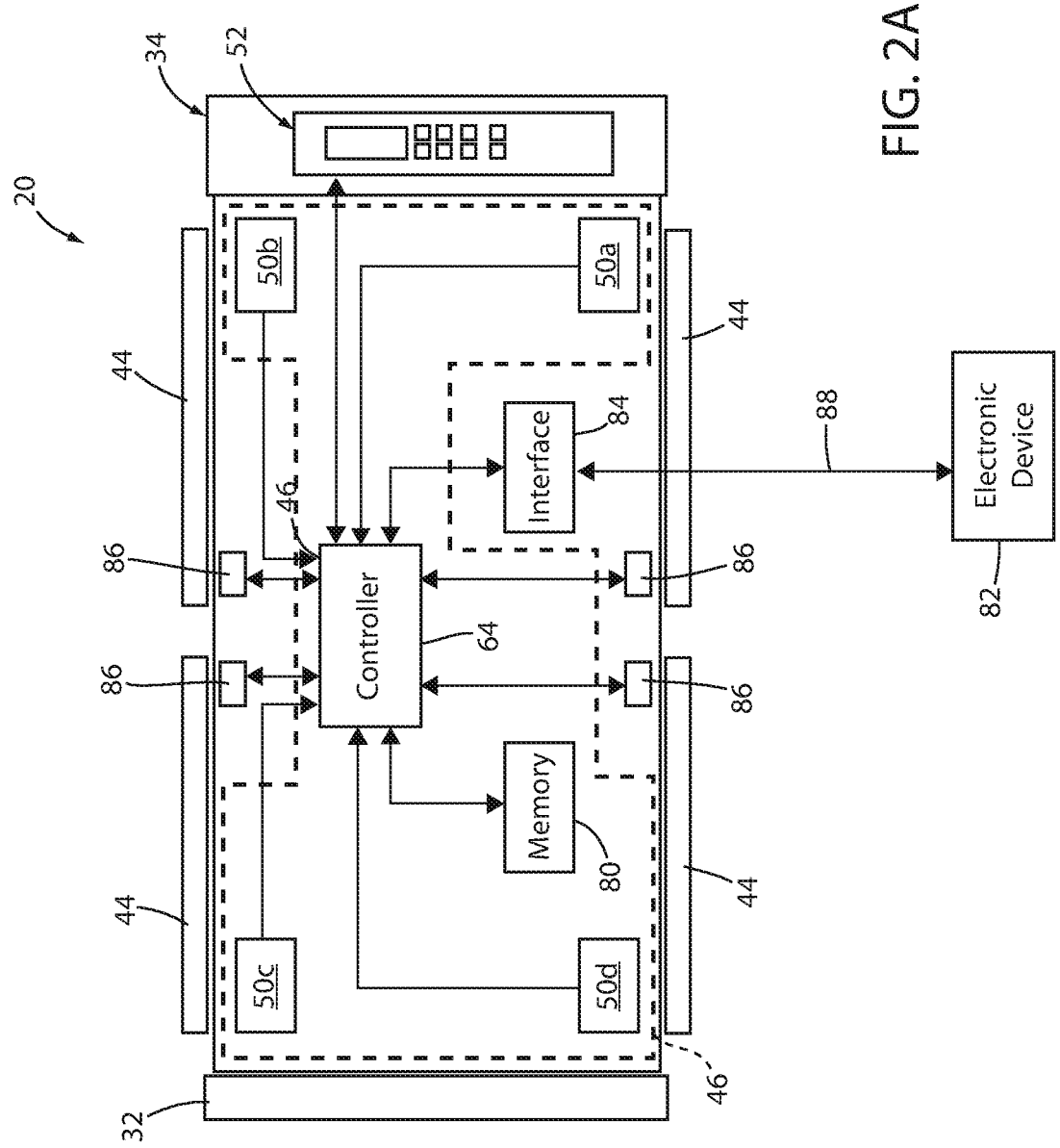
FIG. 2A is a diagram of the person support apparatus of FIG. 1 showing a second embodiment of an exit detection system that may be incorporated therein.

In another embodiment, exit detection system 46 is constructed in the manner illustrated in FIG. 2A. As shown therein, exit detection system 46 includes four load cells 50a-d that are mounted to frame 28 in a manner such that they support, and detect, the weight of the deck 30 and any objects or occupants positioned thereon. In one embodiment, load cells 50a-d are mounted to lift header assemblies (not shown) attached to the upper ends of elevation adjustment mechanisms 26 and support the entire weight of the frame 28, in addition to support deck 30. One detailed manner of implementing this mounting arrangement is shown in detail in the Stryker Maintenance Manual for the MedSurg Bed, Model 3002 S3, published in 2010 by Stryker Corporation of Kalamazoo, Mich., the complete disclosure of which is incorporated herein by reference. Other load cell mounting arrangements are also possible.

Load cells 50a-d are each communicatively coupled to a controller 64 that receives and analyzes the outputs of load cells 50a-d in the manners described in greater detail below. Controller 64 is constructed of any electrical component, or group of electrical components, that are capable of carrying out the functions described herein. In many embodiments, controller 64 is a conventional microcontroller, although not all such embodiments need include a microcontroller. In general, controller 64 includes any one or more microprocessors, microcontrollers, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controller 64 in carrying out the functions described herein, as well as the data necessary for carrying out these functions, are stored in a memory 80 accessible to controller 64.

Although not shown in FIG. 2, exit detection system 46 includes a controller that, in at least one embodiment, is physically the same as controller 64 and is also programmed to carry out the same occupant motion analysis algorithms as controller 64 of FIG. 2A. The controller of exit detection system 46, however, differs from controller 64 in that it is adapted to process the outputs of one or more sensors that are of a different kind of sensor than the load cells 50*a-d* of FIG. 2A. In other embodiments, the controller of exit detection system 46 may differ from controller 64. As will be discussed in greater detail below, controller 64 is adapted to monitor the movement and location of a person supported on support deck 30 and to initiate an alarm if the person moves in a manner indicative of an imminent departure or exit from the person support apparatus 20.

In the embodiments shown in FIGS. 2 and 2A, exit detection system 46 is in communication with a control panel 52 mounted to footboard 34. Control panel 52 includes a plurality of controls 54—which may be buttons, dials, switches, or other devices—one or more of which allows a user to control various aspects of exit detection system 46. Control panel 52 may also include a display 56 for displaying information regarding exit detection system 46. In some embodiments, display 56 is a touch screen display, while in other embodiments it is a display without any touch sensitivity. Although FIGS. 2 and 2A both illustrate control panel 52 mounted to footboard 34, it will be understood that one or more additional controls panels can be added to person support apparatus 20 in different locations, such as the siderails 44, for controlling various aspects of exit detection system 46.

In one embodiment, controls 54 of control panel 52 enable a user to turn exit detection system 46 on and off, as well as allowing a user to select different sensitivity levels or zones which are used for triggering an exit alert, as will be discussed in greater detail below. In at least some embodiments, controls 54 also allow a user to configure the alerting features of exit detection system 46, including choosing from amongst the different types of alerts that can be issued by exit detection system 46. Such types include local alerts (issued at person support apparatus 20), remote alerts (issued at a remote location, such as a nurse's station, hallway light, or to mobile communication devices carried by personnel), audio alerts, visual alerts, and/or any combinations of these.

Figure 3:
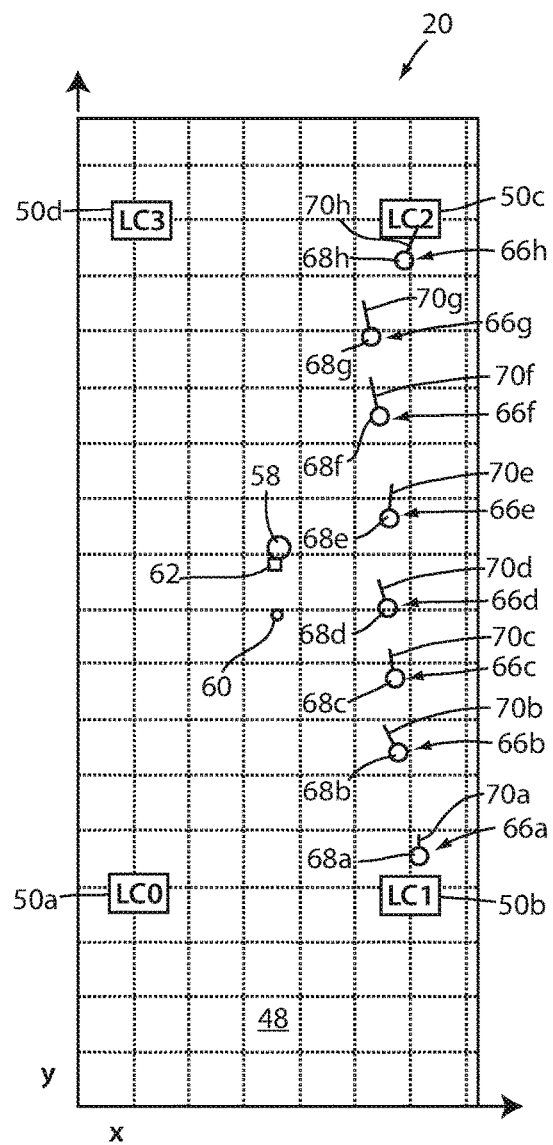
FIG. 3 is a plan view a support surface of the person support apparatus of FIG. 1 illustrating movement of an object's center of gravity from a first point (LC1) to a second point (LC2)
Figure 4:
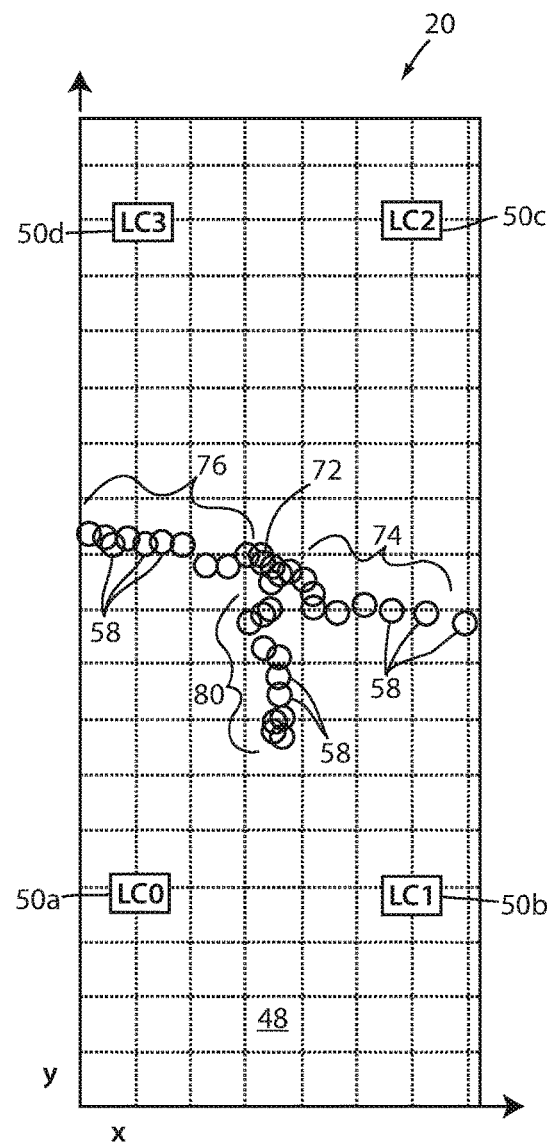
FIG. 4 is a plan view of the support surface of the person support apparatus of FIG. 1 illustrating movement of an occupant's center of gravity as the occupant rolls left, rolls right, and sits up.

FIGS. 3 and 4 illustrate in greater detail the type of occupant position and movement monitoring that is performed by exit detection system 46 in at least one embodiment. More specifically, FIGS. 3 and 4 illustrate a plan view diagram of support surface 48 in an embodiment of person support apparatus 20 in which exit detection system 46 includes load cells 50*a-d*. Although load cells 50*a-d* are positioned underneath support deck 30 in some embodiments, load cells 50*a-d* are visible in FIGS. 3 and 4 in order to illustrate their relative lateral and longitudinal positions with respect to the lateral and longitudinal dimensions of support surface 48. FIG. 3 also illustrates a geometric center 62 of the load cells 50*a-d*, a geometric center 60 of the entire support surface 48, and a center of gravity 58 detected by load cells 50*a-d* when no objects or occupants are positioned on top of support surface 48.

Controller 64 of exit detection system 46 is adapted to determine the center of gravity of whatever load is applied to support surface 48. In other words, exit detection system 46 determines the center of gravity of the combined weight of an occupant, mattress, and/or any objects that are positioned on support surface 48. In one embodiment, exit detection system 46 determines this center of gravity using the algorithm disclosed in commonly assigned U.S. Pat. No. 5,276,432 issued to Travis and entitled PATIENT EXIT DETECTION MECHANISM FOR HOSPITAL BED, the complete disclosure of which is incorporated herein by reference. In other embodiments, other algorithms may be used.

Exit detection system 46 is not only adapted to determine a current location of the center of gravity of the total load on support surface 48, it is also adapted to repetitively determine this location, compare changes in this location over time, and repetitively determine a speed and direction of movement of the center of gravity. For example, FIG. 3 includes a plurality of indicators 66*a-h* that each includes a circle 68 and a tail 70. Indicators 66*a-h* identify the locations of the center of gravity detected by exit detection system 46 as an object having a constant weight is moved in a generally straight line from an initial position adjacent load cell 50*b* to a final position adjacent load cell 50*c*. The circle 68 of each indicator 66 identifies the location of the center of gravity while the tail identifies both the speed and direction of movement of the center of gravity. More specifically, the length of the tail 70 is proportional to the determined speed, and the orientation of the tail 70 is aligned with the direction of movement.

In one embodiment, the controller of exit detection system 46 (such as controller 64) computes the speed and direction of movement of the center of gravity by comparing successive determinations of position, measuring the elapsed time between the successive determinations of position, and determining the speed of movement in both the x and y directions by dividing the movement in each of these directions by the elapsed time between two successive determinations of position. Thus, for example, with specific reference to FIG. 3, exit detection system 46 determines the speed and direction of movement associated with indicator 66*c* by comparing how far position indicator 66*c* has changed in both the x and y directions with respect to position indicator 66*b*. In the illustrated embodiment of FIG. 3, the x direction refers to the horizontal direction while the y direction refers to the vertical direction. Exit detection system 46 also monitors or determines the amount of time that has elapsed between the load cell measurements that were used to determine the positions of indicators 66*b* and 66*c*. From this information, the speed in both the x direction and y direction is determined. A straight line passing through indicators 66*b* and 66*c* indicates the direction of movement and thus defines the orientation of tail 70 of indicator 66*c*.

The particular units that are used to measure the speed can be varied. For example, the speed can be measured in inches per second, centimeters per second, or other units of measurement. In at least one embodiment, the speed can be computed using unitless measurements of distance. For example, the distance in both the x and y direction can be determined based on a grid wherein the actual physical distance between lines of the grids is not measured. As one example, the grid lines may correspond to predetermined fractions or percentages of the total width (x direction) and height (y direction) of support surface 48.

Exit detection system 46 is also adapted, in at least one embodiment, to analyze the movement of the occupant's position and determine whether and when an occupant has rolled over to his or her right or left, as well as to determine whether and when an occupant has moved from a lying position to a sitting position. Such analysis is carried out by monitoring the lateral and longitudinal movement of the occupant's center of gravity. For example, FIG. 4 illustrates three different types of movement of an occupant whose initial position, while lying substantially flat on support surface 48, is at position 72. More specifically, position sequence 74 illustrates the successive centers of gravity 58 of an occupant who has rolled from initial position 72 to his or her left and onto his or her left side (the head end of support surface 48 is toward the top of the page in FIG. 4). Position sequence 76 illustrates the successive centers of gravity 58 of an occupant who has rolled from initial position 72 to his or her right and onto his or her right side. Position sequence 78 illustrates the successive centers of gravity 58 of an occupant who initially is lying down on support surface 48 at initial position 72 and sits up.

Controller 64 of exit detection system 46 determines whether a person has rolled onto one of his or her sides by monitoring both the lateral and longitudinal movement of the person's center of gravity. If the movement is primarily lateral movement (e.g. left to right, or along the x-axis, in FIGS. 3 and 4), with little or no change in the longitudinal position of the center of gravity—such as is illustrated in position sequences 74 and 76 of FIG. 4—then controller 64 concludes that the person has rolled onto his or her side. If the lateral movement of the person is also accompanied by a significant amount of longitudinal movement, the controller 64 concludes that the person is not rolling, but is moving in another manner (e.g. sitting up, moving one or more legs off the edge of the mattress, etc.). Controller 64, in at least one embodiment, is adapted to not issue an exit alert when it determines that the occupant of person support apparatus 20 is merely rolling onto his or her right or left sides.

Controller 64, however, is adapted to record in memory 80 the event of an occupant rolling onto his or her side, or an occupant rolling from his or her side back onto his or her back, or an occupant sitting up or down. Still further, controller 64 is adapted in at least one embodiment to forward this information to an electronic device 82 that is located off of person support apparatus 20. Controller 64 forwards this information via an interface 84 that is in communication with the electronic device 82 via a communication link 88 (FIGS. 2 and 2A). In one embodiment, electronic device 82 is a server coupled to a healthcare network, communication link 88 is a wireless link, and interface 84 is a WiFi (e.g. IEEE 802.11) radio adapted to communicate wirelessly with a healthcare Ethernet via one or more access points. In other embodiments, electronic device 82 is an electronic medical records server or computer, and controller 64 forwards information about the occupant's rolling and/or sitting up/down to the electronic medical records server or computer. The information includes the time of the rolling and/or sitting up/down, the direction of rolling, and the duration of the rolling and/or sitting up/down. In still other embodiments, interface 84 is an Ethernet port and communications link 88 is a wired Ethernet cable that couples either directly to electronic device 82 or to a network that is in communication with device 82. Still other variations are possible.

In addition to determining and recording when an occupant sits up and/or rolls over while positioned on person support apparatus 20, controller 64 is further adapted to continuously determine what state the occupant is in. The various states that controller 64 monitors include: sitting up, lying down, on back, on right side, on left side, and/or any other states that may be desirable to monitor. This information is used, in at least some embodiments, by controller 64 when determining whether to issue an exit alert, as will be described in greater detail below.

Exit detection system 46 (FIGS. 2 and 2A) is further adapted to communicate with a plurality of siderail sensors 86. Siderail sensors 86 may be any conventional siderail sensors that are adapted to detect whether an associated siderail 44 is in an up position, a down position, or an intermediate position. Exit detection system 46 is adapted to utilize the current status of the siderails 44 (e.g. up, down, or an intermediate position) in determining whether to issue an exit alert based upon the movement of the occupant of person support apparatus 20. Generally speaking, and as will be described in greater detail below, exit detection system 46 will not issue an exit alert if the occupant's movement is toward a siderail 44 that is in an up condition. Alternatively, exit detection system 46 will issue an exit alert if the occupant's movement is toward a siderail that is up, but exit detection system 46 will use a more stringent set of criteria before issuing the alert in those situations. If exit detection system 46 determines that the occupant is moving toward a siderail that is currently in a down position, exit detection system 46 will issue an exit alert if the movement of the occupant meets other criteria, as described more below.

Figure 5:
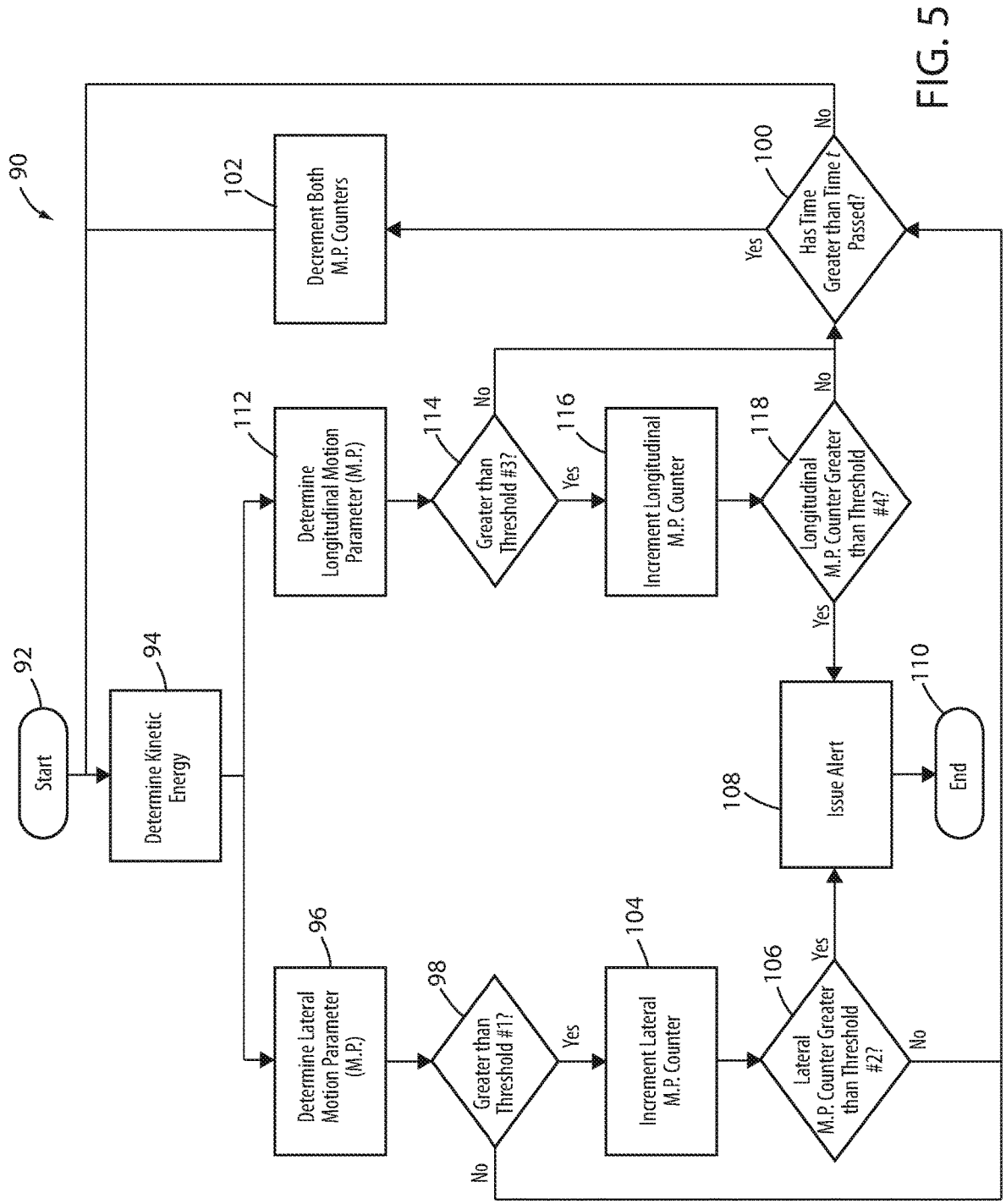
FIG. 5 is a flow diagram of an illustrative alert algorithm that may be implemented by the person support apparatus of FIG. 1.

FIG. 5 is a flow diagram of an illustrative exit alert algorithm 90 that is implemented, in at least one embodiment, by controller 64 of exit detection system 46. Exit alert algorithm starts at step 92 when it is activated by a user utilizing control panel 52. That is, control panel 52 includes one or more controls 54 that enable a user to turn on and off exit alert algorithm 90. Alert algorithm 90 starts at start step 92 when a user turns it on. At a next step 94, controller 64 determines the current kinetic energy of the occupant of person support apparatus 20 utilizing load cells 50$a$-$d$, or whatever other sensors exit detection system 46 may utilize for detecting and monitoring the occupant's movement. Controller 64 determines the occupant's kinetic energy by computing both the occupant's current velocity and his or her weight. This information is then used to compute the kinetic energy using the formula K.E.=½ mv$^2$, where "K.E." is the kinetic energy, "m" is the occupant's mass (or, in this embodiment, the occupant's weight is used as a proxy for his or her mass); and "v" is the current velocity of the occupant.

It will be understood by those skilled in the art that the term "kinetic energy" as used herein refers to not only the quantity that is equal to one-half multiplied by the occupant's mass (or weight) and further multiplied by the square of the occupant's velocity, but also all other quantities that are mathematically directly proportional to this quantity. That is, for example, the term "kinetic energy" also encompasses the product of the occupant's mass multiplied by the square of the occupant's velocity without further multiplying this product by a constant of one-half. Any other quantity that is directly proportional to ½ mv$^2$ will also be understood to qualify as the occupant's "kinetic energy," as that term is used herein.

Controller 64 determines the occupant's velocity by taking at least two successive measurements of the occupant's center of gravity, determining the distance between the two successive measurements, and then dividing this distance by the time that has elapsed during the interval between the two successive measurements. Controller 64 determines the occupant's weight (used as a proxy for the occupant's mass) in at least one embodiment by directly measuring the occupant's weight using load cells 50$a$-$d$. For example, in at least one embodiment, controller 64 is programmed to carry out any of the scale functions disclosed in commonly assigned, U.S. patent application Ser. No. 14/212,367 filed Mar. 14, 2014 by inventors Michael Joseph Hayes et al. and entitled PATIENT SUPPORT APPARATUS WITH PATIENT INFORMATION SENSORS, the complete disclosure of which is hereby incorporated herein by reference. Such functions include, but are not limited to, auto-zeroing the loads sensed by load cells 50a-d such that an occupant's weight may be determined automatically by exit detection system 46 without requiring a user to zero the load cell readings, or take any other steps in order to determine the occupant's weight. In another embodiment, the occupant's weight is determined after a user manually zeroes the load cells 50a-d, or other weight detection sensors, and/or after the user manipulates the appropriate control 54 on control panel 52 causing controller 64 to take an occupant weight reading. In still other embodiments, the occupant's weight is entered into memory 80 by a caregiver either through manual manipulation of control panel 52, or it is communicated electronically to person support apparatus 20 from electronic device 82 (which may be an electronic medical records server) via communication link 88. Still other methods of determining the occupant's weight are also possible.

After determining the occupant's kinetic energy at step 94, controller 64 moves to step 96 where it determines a lateral motion parameter. The lateral motion parameter determined at step 96 is a parameter that is based on the component of the kinetic energy determined at step 94 that is with lateral movement of the occupant (i.e. along the x direction in FIGS. 3 and 4). In other words, controller 64 determines how much of the kinetic energy determined at step 94 is due to movement of the occupant in the lateral direction and how much is due to movement in the longitudinal direction. The component of the kinetic energy that is determined to be due to longitudinal movement is utilized in step 112, as will be discussed in greater detail below. The lateral component of the kinetic energy can be determined in any conventional manner, such as by determining the ratio between the lateral component of the occupant's velocity and the longitudinal component of the occupant's velocity. Other methods are also possible.

In addition to determining the lateral component of the occupant's kinetic energy, controller 64 also performs one or more additional calculations at step 96, in at least one embodiment. Specifically, in at least one embodiment, controller 64 further takes the lateral component of the kinetic energy and normalizes this value. The normalized value is then used as the lateral motion parameter. Various normalization techniques may be used.

After determining the lateral motion parameter at step 96, controller 64 moves to step 98 where it compares the lateral motion parameter computed at step 96 to a first threshold. The first threshold used at step 98 is a pre-set threshold that is used to filter out small motions and/or transient artifacts detected in the movement of the occupant and can be set to various suitable values. If controller 64 determines at step 98 that the lateral motion parameter does not exceed the first threshold, controller 64 moves to step 100 where it determines how much time has passed since it last decremented both a lateral motion counter and a longitudinal motion counter (both of which will be discussed in greater detail below). If that elapsed time exceeds a time threshold "t," then controller 64 moves onto step 102, where it decrements both the lateral motion parameter counter and the longitudinal motion parameter counter, both of which will be discussed in greater detail below. If the elapsed time period is less than the time threshold "t," then controller 64 returns to step 94 where it re-measures the occupant's kinetic energy and follows the steps subsequent to step 94.

If controller 64 determines at step 98 (FIG. 5) that the currently measured lateral motion parameter exceeds the first threshold, controller 64 proceeds to step 104. At step 104, controller 64 increments a lateral motion parameter counter. The lateral motion parameter counter is a counter that is maintained by controller 64 and updated as the occupant moves. As will be described more below, it is utilized as part of a "leaky bucket" algorithm followed by controller 64 in determining whether to issue an exit alert or not.

After incrementing the lateral motion parameter counter at step 104, controller 64 moves to step 106 where it determines whether the lateral motion parameter counter exceeds a second threshold. If the current value of the lateral motion parameter counter exceeds the second threshold, controller 64 moves to step 108, where it issues an exit alert. The exit alert may take on any suitable form. In one embodiment, the exit alert includes an aural alert issued from a speaker, buzzer, or other sound-generating device on person support apparatus 20 that is under the control of exit detection system 46, or in communication with exit detection system 46. In another embodiment, controller 64 also issue a remote alert, such as at a nurses' station, or other location, where one or more caregivers who may be assigned to care for the occupant of person support apparatus 20 are located. The remote alert is carried out via interface 84 and communication link 88. In one embodiment, interface 84 is a nurse-call cable port on person support apparatus 20 and communication link 88 is a nurse-call cable that plugs into person support apparatus 20 and communicatively couples person support apparatus 20 to an existing nurse-call system within a given facility. In other embodiments, communication link 88 may be wireless connection that communicates with the nurse-call system, or other devices. In still another embodiment, person support apparatus 20 is configured to allow a user to choose whether the exit alert is local and/or remote, as well as to choose characteristics of the exit alert (e.g. the volume and/or tone of an aural exit alert). After issuing the exit alert, controller 64 ends alert algorithm 90 at step 110 until it is once again re-started in response to a users command.

If controller 64 determines at step 106 that the current lateral motion parameter counter does not exceed the second threshold, controller 64 moves onto to step 100 without issuing an exit alert and proceeds in the manner previously described above for step 100.

Either substantially simultaneously with, or sequentially with, the performance of steps 96, 98, 104, and 106, controller 64 carries out a similar set of steps that are based on the longitudinal movement of the occupant at steps 112-118. More specifically, at step 112, controller 64 determines a longitudinal motion parameter. The longitudinal motion parameter is the same as the lateral motion parameter determined at step 96 but based on the component of the occupant's movement in the longitudinal direction (y direction in FIGS. 3-4), rather than the lateral direction. That is, controller 64 determines at step 112 how much of the kinetic energy determined at step 94 is due to movement of the occupant in the longitudinal direction. This longitudinal component of the kinetic energy can be determined in any conventional manner, such as by determining the ratio between the lateral component of the occupant's velocity and the longitudinal component of the occupant's velocity. Other methods are also possible.

In addition to determining the longitudinal component of the occupant's kinetic energy, controller 64 also performs one or more additional calculations at step 112, in at least one embodiment. Specifically, in at least one embodiment, controller 64 further takes the longitudinal component of the kinetic energy and normalizes this value in the same manner that controller 64 normalizes the lateral component of the kinetic energy in step 96. The normalized value is then used as the longitudinal motion parameter. Various normalization techniques may be used.

After determining the longitudinal motion parameter at step 112, controller 64 moves onto step 114 where it compares the longitudinal motion parameter computed at step 112 to a third threshold. The third threshold used at step 114 is a pre-set threshold that is used to filter out small motions and/or transient artifacts detected in the movement of the occupant and can be set to various suitable values. In one embodiment, the third threshold of step 114 is the same as the first threshold of step 98. In other embodiments, the first and third thresholds are different.

If controller 64 determines at step 114 that the longitudinal motion parameter does not exceed the third threshold, controller 64 moves to step 100 where it determines how much time has passed since it last decremented both the longitudinal motion counter and a longitudinal motion counter. If that elapsed time exceeds a time threshold "t," then controller 64 moves onto step 102, where it decrements both the longitudinal motion parameter counter and the longitudinal motion parameter counter. If the elapsed time period is less than the time threshold "t," then controller 64 returns to step 94 where it re-measures the occupant's kinetic energy and follows the steps subsequent to step 94.

If controller 64 determines at step 114 (FIG. 5) that the currently measured longitudinal motion parameter exceeds the third threshold, controller 64 proceeds to step 116. At step 116, controller 64 increments a longitudinal motion parameter counter. The longitudinal motion parameter counter is a counter that is maintained by controller 64 and updated as the occupant moves. As will be described more below, it is utilized as part of the previously mentioned "leaky bucket" algorithm followed by controller 64 in determining whether to issue an exit alert or not.

After incrementing the longitudinal motion parameter counter at step 116, controller 64 moves to step 118 where it determines whether the longitudinal motion parameter counter exceeds a fourth threshold. If the current value of the longitudinal motion parameter counter exceeds the fourth threshold, controller 64 moves to step 108, where it issues an exit alert. The exit alert may take on any suitable form, as discussed above. The fourth threshold used in step 116, in at least one embodiment, is different than the second threshold used in step 106. More specifically, in at least one embodiment, the fourth threshold of step 118 is set higher than the second threshold of step 106. This higher value accounts for the fact that occupants of person support apparatus 20 are less likely to exit from person support apparatus 20 via either its head end or foot end due to both the difficulty of exiting in either of these fashions, as well as the typical presence of headboard 32 and footboard 34. Consequently, movement in the longitudinal direction, which is aligned with the headboard 32 and footboard 34, will require surpassing a higher threshold than movement in the lateral direction before an alert is issued at step 108, in at least one embodiment.

If controller 64 determines at step 118 that the current longitudinal motion parameter counter does not exceed the fourth threshold, controller 64 moves onto to step 100 without issuing an exit alert and proceeds in the manner previously described above for step 100.

From the foregoing description of exit alert algorithm 90, it can be seen that controller 64 executes a version of a leaky bucket algorithm for both the lateral and longitudinal components of the occupant's movement. That is, controller 64 keeps track of a running total of both the lateral motion parameter counter (used in step 106) and the longitudinal motion parameter counter (used in step 118), and increments either of these whenever motion in the lateral and/or longitudinal directions is detected that exceeds the first and third thresholds (steps 98 and 106 for the lateral motion) and/or the second and fourth threshold (steps 114 and 118 for the longitudinal motion). Exit alert algorithm 90 is repeated multiple times a second so that if an occupant makes a significant movement in either the lateral or longitudinal directions, it will not take long for one or more of the lateral and longitudinal counters to exceed their respective second and fourth thresholds, thereby resulting in an exit alert (step 108). The counters of steps 106 and 118 therefore represent the bucket.

The "leak" in the bucket is represented by step 102. As time passes, the counters are automatically decremented at step 102. This achieves the effect of issuing an alert at step 108 based primarily upon more recent and larger amounts of kinetic energy of the occupant, rather than previous movements and/or movements having less kinetic energy. Occupant shifting that is not preparatory to a departure from person support apparatus 20 is unlikely to trigger an alert at step 108, and—to the extent this shifting movement increments either of the counters at steps 106 or 108—this incrementing will be decremented over time through the "leaking" action of step 102. The rate at which the counters are decremented at step 102 can vary according to several factors, including, but not limited to, the speed at which exit alert algorithm 90 is repeated, the values of the first and third thresholds (steps 98 and 114, respectively), as well as other factors.

In at least one embodiment, controller 64 is adapted to modify one or more of the thresholds based upon other factors or conditions of person support apparatus 20. For example, in one embodiment, controller 64 modifies the second threshold of step 106 if the siderails 44 nearest to the occupant's center of gravity are both in an up position or both in a down position. If they are both in an up position, controller 64 sets the second threshold used at step 106 to a higher value, and if they are both in a down position, controller 64 sets the second threshold used at step 106 to a lower value. This has the effect of requiring a greater amount of kinetic energy to trigger an exit alert when the kinetic energy is expended in the direction of the up siderail than when the kinetic energy is expended in the direction of a down siderail. The higher threshold for triggering an exit alert when the siderail is in the up position, rather than the down position, reflects the fact that an occupant of person support apparatus 20 is less likely to exit person support apparatus 20 by climbing over a raised siderail 44 than by exiting over a lowered siderail, as well as the fact that—to the extent the occupant did attempt to exit over a raised siderail—a greater amount of movement would likely be required of the occupant than would be necessary if the occupant were to exit over a lowered siderail.

In still another embodiment, exit alert algorithm 90 is modified to utilize separate lateral motion parameter counters for each lateral direction. In other words, controller 64 maintains and updates a first lateral motion parameter for occupant movement towards a right side of person support apparatus 20, and maintains and updates a second lateral motion parameter for occupant movement towards a left side of person support apparatus 20. That is, steps 96, 98, 104, and 106 are modified to include right and left lateral motion parameters, and right and left lateral motion parameter counters. Step 102 is also modified to decrement both the left and right lateral motion parameter counters. By maintaining separate first and second lateral motion parameters, controller 64 can more easily account for situations where a siderail 44 is raised on one side of person support apparatus 20, but lowered on the opposite side. In those situations, controller 64 will utilize a higher threshold at step 106 for lateral movement toward the raised siderail, while utilizing a relatively lower threshold at step 106 for lateral movement towards a lowered siderail. Controller 64 determines the current state of a siderail 44 based upon information from siderail sensors 86.

In a similar manner, controller 64 may also utilize separate head end and foot end longitudinal motion parameters and the corresponding head end and foot end longitudinal motion parameter thresholds may be varied based upon the absence or presence of the headboard 32 and footboard 34. In such an embodiment, person support apparatus 20 includes a footboard sensor adapted to detect the presence or absence of a removable footboard 3. Person support apparatus 20 may also include a headboard sensor adapted to detect the presence or absence of headboard 32 (to the extent it is removable).

In another embodiment, exit alert algorithm 90 is modified to take into account the occupant's current center of gravity relative to the position of the siderails 44. This current location of the center of gravity is used to adjust the motion counter thresholds used at steps 106 and/or 118 if the current location moves from a location next to a raised siderail to a location next to a lowered siderail, or vice versa. For example, in one embodiment, if an occupant's current location is located in an upper region of support deck 30 where both of the adjacent head end siderails 44 are in the up position, and the occupant's location shifts to a lower region of the support deck where one or more of the foot end siderails 44 are in the lowered position, controller 64 is adapted to adjust the lateral motion parameter threshold(s) to a lower value.

In yet another embodiment, controller 64 is adapted to follow a modified exit alert algorithm that takes into account the current angle of the head section 36 relative to horizontal. In at least one embodiment, controller 64 uses higher threshold values for the lateral motion parameter counter comparison of step 106 if the current location of the occupant's center of gravity is close to head section 36 and head section 36 is raised beyond a threshold value. This changed threshold value at step 106 takes into account the fact that an occupant of person support apparatus 20 is unlikely to exit from head section 36 if head section 36 is pivoted upwardly a significant amount. Instead, if head section 36 is pivoted upwardly a significant amount, the location of the occupant's center of gravity during an exit is likely to lie much closer to thigh section 40 or foot section 42. Accordingly, an occupant's movement toward the left or right side of head section 36 while head section 36 is pivoted upwardly is more likely to be the result of the occupant shifting positions on person support apparatus 20 than the result of him or her intending to exit person support apparatus 20.

In still another embodiment, controller 64 is configured to keep track of not only the occupant's location, but also his or her orientation on support deck. In other words, controller 64 determines and records whether the occupant is currently sitting up, lying down, on his or her right or left side, etc. Controller 64 further adjusts the thresholds used in 106 and 118 based upon the current orientation of the occupant. Thus, for example, if occupant is currently lying down, controller 64 uses higher thresholds for triggering an exit alarm because it is less likely that an occupant will exit person support apparatus 20 without first sitting up. Similarly, if the occupant remains on his or her back, higher thresholds may continue to be used by controller 64 because it is less likely that an occupant will exit without first rolling from his or her back onto one of his or her sides.

In still another embodiment, control panel 52 is adapted to include one or more controls 54 that enable a user of person support apparatus 20, such as a caregiver, to manually adjust any one or more of the thresholds used in exit alert algorithm 90. This enables a user to adjust the sensitivity of the exit alert algorithm. If the user does not want to be provided with an alert unless a significant amount of movement has occurred, he or she can accomplish this by choosing one or more higher thresholds. Conversely, if he or she wants to be notified of even small occupant movements, he or she can use controls 54 to set the thresholds to a lower value.

In still another embodiment, controller 64 is adapted to modify exit alert algorithm based upon occupant-specific data provided to it, or gathered by it over time. For example, if a person support apparatus 20 is used in a hospital or healthcare setting and the occupants are typically patients, information pertaining the mobility and/or restlessness of a particular patient is input into exit detection system 46 and used by controller 64 to adjust one or more of the thresholds in order to better accommodate that particular patient. The information comes from an electronic medical record communicated to person support apparatus 20 via communication link 88, or it comes from information directly entered into person support apparatus 20 via control panel 52. In still another embodiment, controller 64 is configured to store data about the movement of the occupant and retain that occupant's movement data over time. From that data, controller 64 adjusts the threshold as appropriate. For example, in one embodiment, controller 64 sets the motion parameter counter thresholds used in steps 106 and/or 118 higher for patients that are restless, as determined by controller 64 from an analysis of the patient's prior movement data.

In still another embodiment, person support apparatus 20 includes one or more controls 54 that allow a user to select different zones on support deck 30 that, when an occupant is about to move out of, will trigger an alert in accordance with algorithm 90. Controller 64 changes one or more of the first through fourth thresholds based on the zone selected by the user, and also examines the current location of the occupant relative to the boundaries of the different zones when carrying out algorithm 90.

It will be understood by those skilled in the art that all of the different features of the different embodiments of exit alert algorithm 90 and/or controller 64 may be separate, or they may be combined in any manner. Thus, for example, in at least one embodiment, controller 64 takes into account not only the status of the siderails 44, but also the angle of the head section 36 and the current position of the occupant's center of gravity when setting the lateral and/or longitudinal motion parameter counter thresholds used in steps 106 and/or 118. Further, in this embodiment, controller 64 takes into account the current orientation of the occupant, and control panel 52 includes controls 54 enabling a user to manually adjust any of the thresholds used in algorithm 90 and/or to select specific zones for triggering an exit alert. Still further, in this embodiment, controller 64 utilizes occupant-specific information when carrying out algorithm 90. In other embodiments, algorithm 90 can be executed with fewer of these features.

In all of the various embodiments, controller 64—whether following exit alert algorithm 90 or some variation of it—is adapted to provide an indication of an occupant's intent to exit person support apparatus 20 prior to the occupant actually exiting. Further, the system and algorithm are adapted to bring about such notification earlier, but with fewer false alarms, than previous exit alerting systems.

In yet another alternative embodiment exit alert algorithm 90 can be modified to use the occupant's momentum rather than kinetic energy. In such an embodiment, step 94 is modified to compute the occupant's momentum (mass times velocity), and the subsequent steps are also modified to calculate and utilize motion parameters that are based on momentum, rather than kinetic energy.

Figure 6:
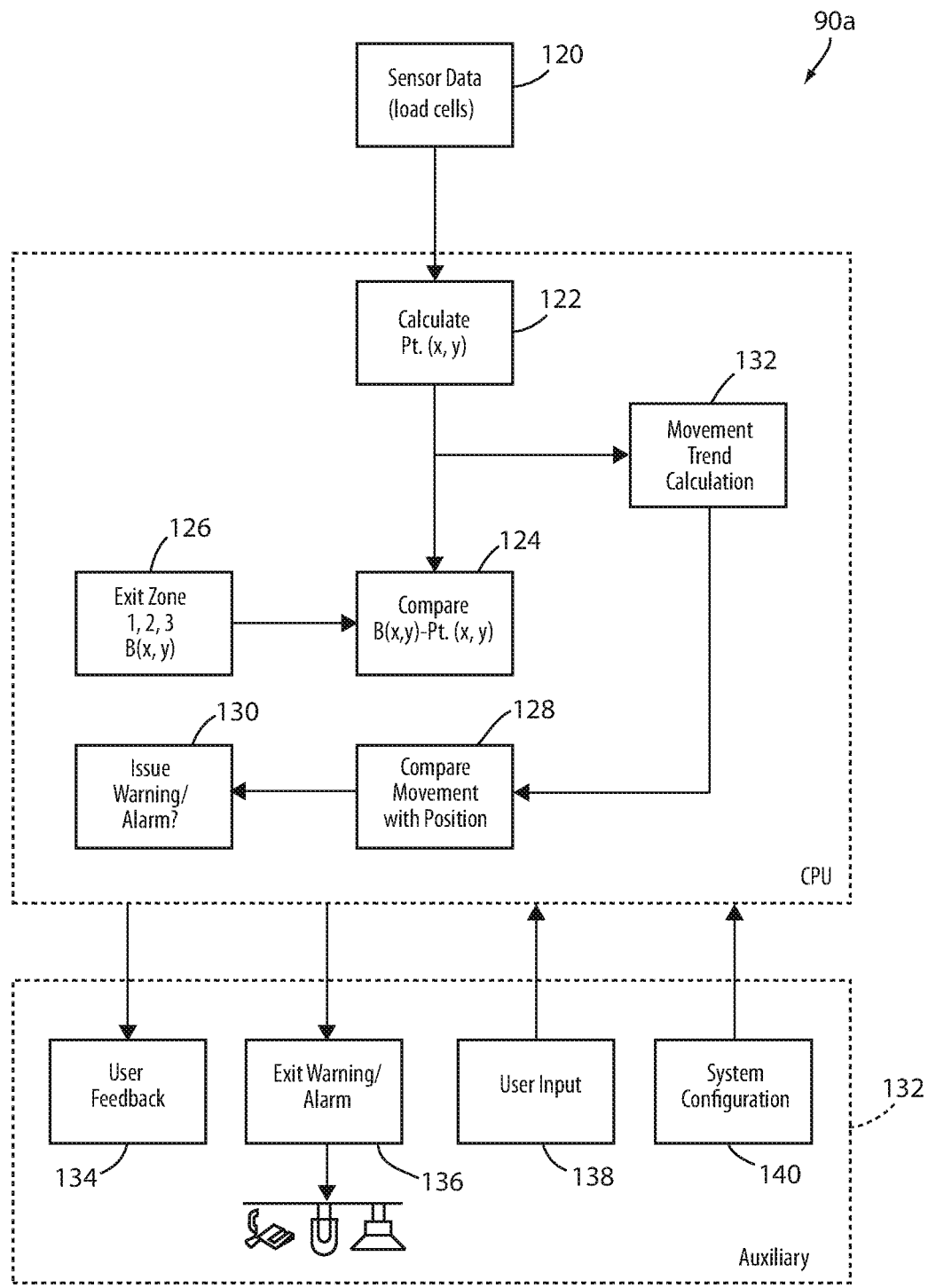
FIG. 6 is a diagram of another alert algorithm that may be implemented by the person support apparatus of FIG. 1.

FIG. 6 illustrates another embodiment of an exit alert algorithm 90a that is implemented by controller 64, or any other controller that is incorporated into exit detection system 46. Exit alert algorithm 90a begins at step 120 where controller 64 takes readings from whatever exit detection sensors person support apparatus 20 is equipped with. For purposes of the following description, it will be assumed that person support apparatus 20 includes load cells 50 for detecting an occupant's departure, but it will be understood by those skilled in the art that other types of sensors may be used, including those discussed previously.

From the readings gathered at step 120, controller 64 proceeds to step 122 where it calculates the point (Pt.(x,y)) where the occupant's center of gravity is currently located. After step 122, controller 64 proceeds to step 124 where it compares the current location of the occupant's center of gravity to one or more boundaries. The boundaries are set up and defined at step 126 through user input, such as via control panel 52. In one embodiment, a user is able to choose one of at least three different zones on person support apparatus 20 that have different boundaries. If the occupant's center of gravity moves outside of the selected zone, or is trending toward moving outside of the selected zone, controller 64 will issue an alert, as discussed in greater detail below. Step 126 therefore allows a user to select the sensitivity of the exit detection system and control how much movement is necessary to trigger an alert.

If controller 64 determines at step 124 that the current center of gravity is outside of the boundary (B(x,y)) of the selected zone, controller 64 skips to step 130 and issues an exit alert. If however, the current center of gravity of the occupant is not outside of the boundary of the selected zone, controller 64 proceeds to step 128 where it compares a trend in the movement of the occupant with the boundaries of the zone. More specifically, after controller 64 has completed step 122 and determined the occupant's location, it also proceeds—in addition to step 124—to step 132 where it determines a trend in the movement of the occupant. In one embodiment, the trend is a determination of the occupant's velocity. In another embodiment, the trend is a determination of the kinetic energy of the occupant, such as described above, in both the lateral and longitudinal directions. In other embodiments, still other types of movement trends are determined. Regardless of the specific type of trend determined, controller 64 determines the trend based upon one or more previous locations of the occupant, the occupant's current location, and the time that has elapsed between the multiple measurements of the occupant's location.

If controller 64 determines at step 128 that the occupant's movement is trending in a manner that is likely to exceed the boundaries of the selected zone (selected at step 126), controller 64 moves to step 130, where it issues an exit alert. In other words, controller 64 does not determine at step 128 whether the occupant's current location is outside of the selected zone (which is done at step 124), but instead analyzes the current trend and determines how likely that the occupant's current position will soon change to be located outside of the selected zone. If the likelihood exceeds a threshold, then controller 64 proceeds to step 130 and issues the alert. Controller 64 therefore performs step 128 in order to anticipate an occupant's movement outside of the selected zone prior to the actual departure, thereby providing an earlier indication to users of the imminent departure. In at least one embodiment, exit alert algorithm 90a is modified to skip step 124 and instead rely only upon step 128 in determining whether to issue an alert at step 130.

Box 132 illustrates various inputs into and outputs from controller 64 when executing exit alert algorithm 90a. More specifically, step 132 provides user feedback 134 to a user, such as a nurse, regarding the monitored movement of the occupant, such movement statistics (e.g. how long since the occupant last moved or turned, how active the occupant has been, how long the occupant has been out of person support apparatus 20, what positions the occupant has been in, etc.). The actual exit alert is issued at step 136 and may be a user-configured combination of audio and visual alerts, as well as a user-configured combination of local and/or remote alerts. User input can be input into controller 64 at step 138, such as information specific to a particular occupant (e.g. weight and/or level of restlessness of the occupant and/or if the occupant has any specific conditions requiring greater or lesser amounts of movement). Step 140 enables system information, such as, but not limited to, the state of the siderails 44 and/or the angle of head section 36, to be input into controller 64 and used in the exit alert algorithm 90a.

Figure 7:
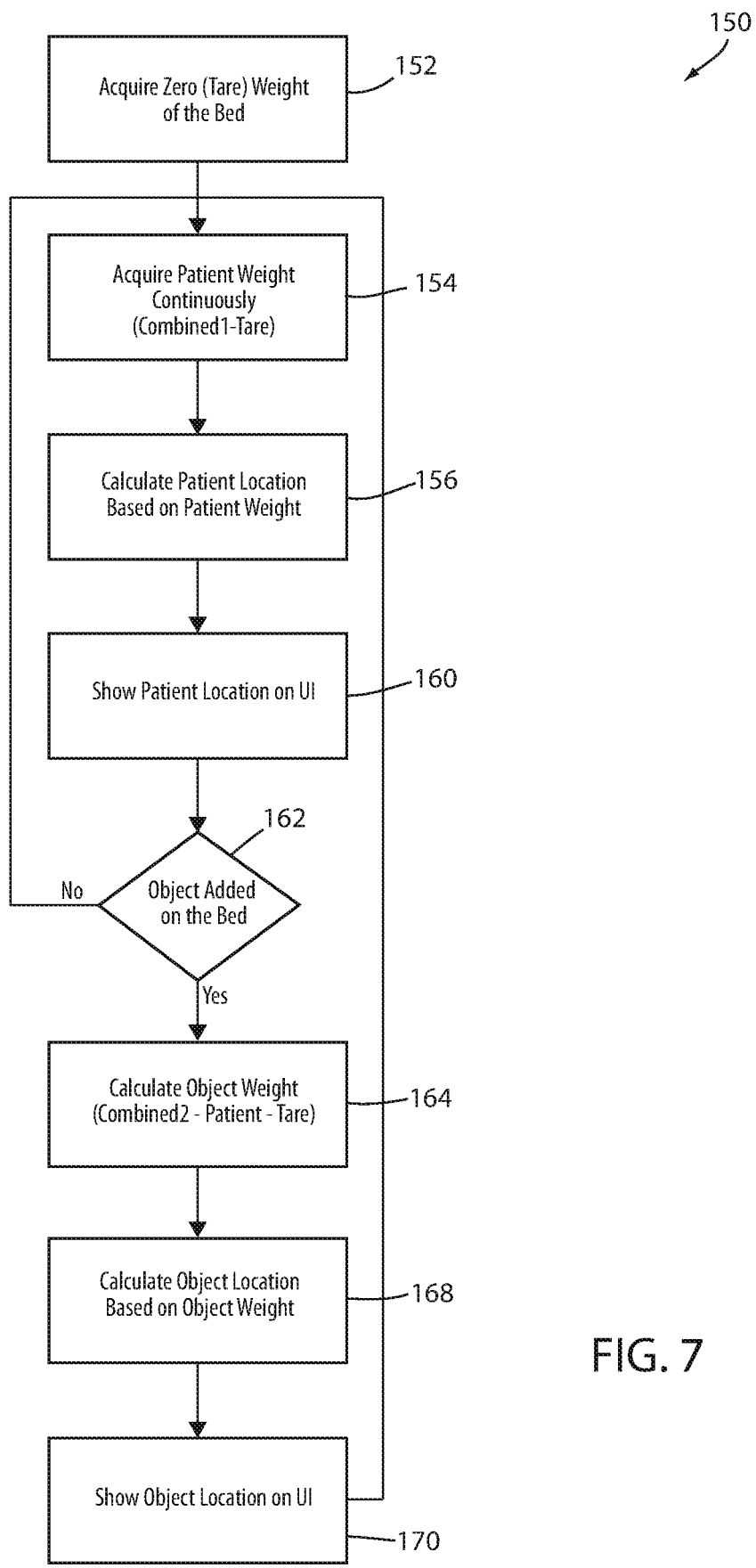
FIG. 7 is a flowchart of an illustrative algorithm for determining an object's location on the person support surface when an occupant is also present thereon.

FIG. 7 illustrates in greater detail a multi-object tracking algorithm 150 that is followed by controller 64 in at least one embodiment. The operation of multi-object tracking algorithm 150 is explained in greater detail below with reference to FIGS. 7-10. Multi-object tracking algorithm 150 is followed, in one embodiment, by a controller 64 that also follows exit alert algorithm 90 or 90a, or any of the variations discussed above. In another embodiment, multi-object tracking algorithm 150 is implemented by controller 64 without also carrying out exit alert algorithm 90 and/or 90a. In still other embodiments of person support apparatus 20, controller 64 is configured to carry out any one of exit alert algorithm 90 and/or 90a without also carrying out multi-object tracking algorithm 150.

Multi-object tracking algorithm 150 begins at step 152 where controller 64 acquires the zero or tare weight of the person support apparatus 20. More specifically, controller 64 acquires the zero or tare weight of those components of person support apparatus 20 that are supported by load cells 50a-d when no occupant is present, such as, but not limited to, support deck 30, a mattress positioned thereon, any bedding that may be on the mattress, etc. As will be discussed below, this tare weight acquisition may occur automatically in one embodiment. Alternatively, person support apparatus 20 may be configured to require a user to manually manipulate one of controls 54 indicating to controller 64 when no occupant is present and when a weight value should be taken. The weight readings taken from load cells 50a-d at that moment are then used as the tare value. In at least one embodiment, tare weight readings are taken for each individual load cell 50a-d, rather than a single cumulative tare weight reading for the combined outputs of the load cells 50a-d. This allows controller 64 to more precisely determine an occupant's position in situations where the center of gravity of an unoccupied support deck 30 is not located at the geometric center of the four load cells.

Figure 8:
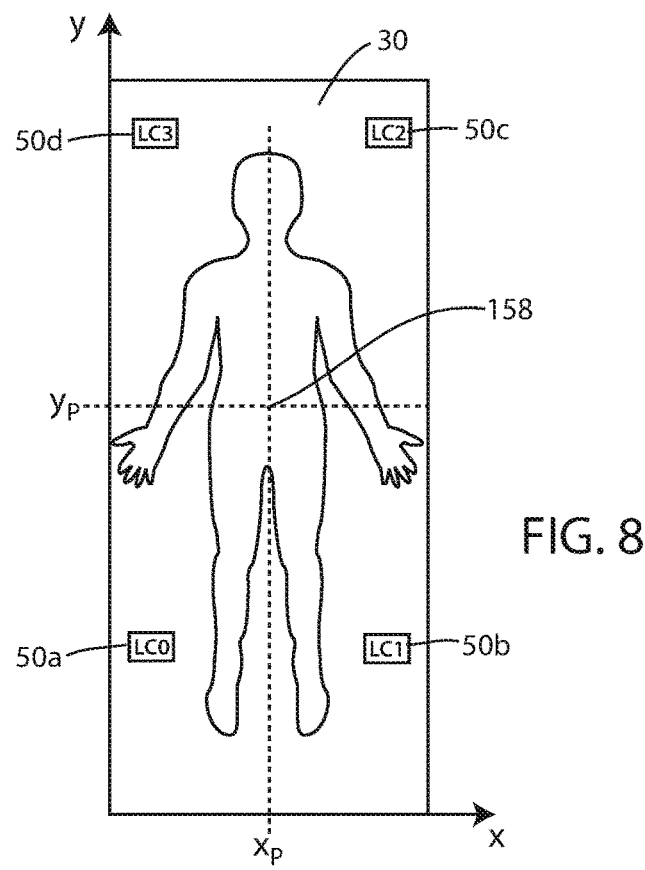
FIG. 8 is a plan view of the support surface of the person support apparatus of FIG. 1 illustrating an occupant in a supine position thereon and having a center of gravity at location $(x_p, y_p)$.

After completing step 152, controller 64 moves to step 154 where it continuously acquires the weight of the patient, or other occupant, of person support apparatus 20 using the outputs from load cells 50a-d, or whatever other occupant detection sensors that may be present on person support apparatus 20. The occupant's weight is calculated by subtracting the tare weight from the total weight readings of the load cells 50a-d. Thereafter, controller 64 moves to step 156 where it determines the location of the occupant, such as a center of gravity 158 of the occupant (FIG. 8). Next, controller 64, in the embodiment illustrated in FIG. 7, proceeds to step 160 where it display the location of the occupant on a user interface, such as display 56 of control panel 52, and/or at a display located at a nurse's station in a healthcare environment, or at some other location remote from person support apparatus 20.

Figure 8A:
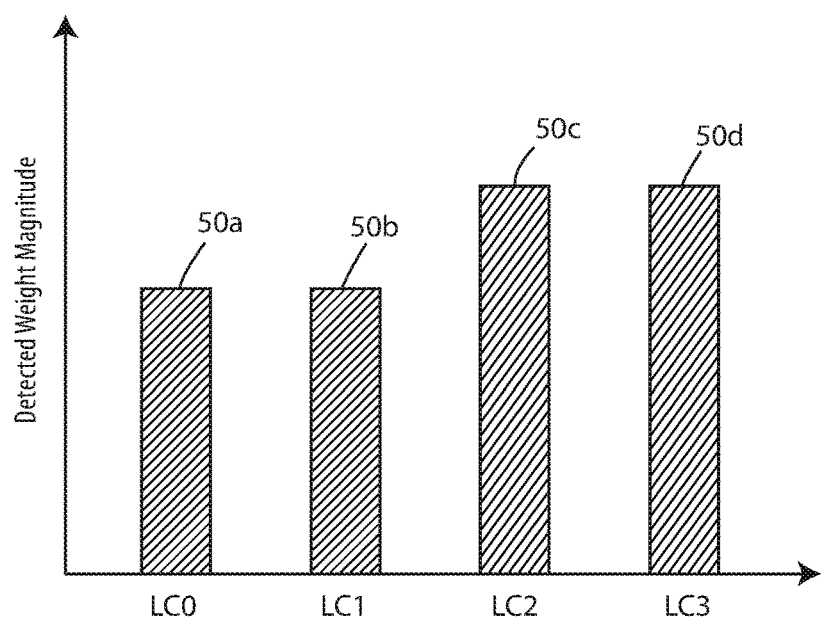
FIG. 8A is a graph illustrating the downward forces detected by the four load cells LC0, LC1, LC2, and LC3 when the occupant of FIG. 8 has his or her center of gravity positioned at location $(x_p, y_p)$.

FIGS. 8 and 8A provide an example of one manner in which controller 64 carries out steps 154 and 156 in algorithm 150. The weight of the occupant on person support apparatus 20 is determined based upon the outputs from the load cells 50a-d. FIG. 8A provides an arbitrary example of the weights sensed by each of the load cells 50a-d when an occupant is positioned on support deck 30 such that his or her center of gravity 158 is located at position $(x_p, y_p)$. The values shown in FIG. 8A are values that result from the patient's weight after the tare weight has been subtracted. In this example, tare weights for each of the load cells 50a-d are individually recorded by controller 64 and the corresponding tare weight value for each individual load cell 50a-d is subtracted from the total weight reading for that individual load cell in order to arrive at the values shown in FIG. 8A.

After completing step 160 (FIG. 7), controller 64 moves to step 162 where it determines whether or not an object 166 (FIG. 9) has been added to support deck 30. Controller 64 carries out step 162 by continuously monitoring the total weight sensed by load cells 50a-d and comparing them to the patient weight (plus the total tare weight of the load cells). To the extent the total sensed weight increases by more than a threshold amount, e.g. a pound or two, and that weight change persists for more than a threshold amount of time (in order to remove transient weight readings due to accelerations from the occupant shifting position), controller 64 concludes that an object 166 has been added to support deck 30. If no object is detected, controller 64 returns to step 154 where it continues to take weight readings in the manner previously described.

If controller 64 detects an object 166 at step 162, it proceed to step 164 where it determines the weight of the detected object 166. This weight is determined by subtracting the patient's weight and the tare weight from the total cumulative weight currently detected by all of the load cells 50a-d. The result is the weight of the object 166. After determining the object's weight at step 164, controller 64 proceeds to step 168 where it determines the location of the object 166.

The location of the object is determined at step 168 by first subtracting from the currently sensed total weight of each of the load cells 50a-d the individual tare weights for each of the four load cells 50a-d, as well as the individual load cell readings 50a-d corresponding to the last calculated position of the occupant on support deck 30. The remaining distribution of the weight of the object 166 among the four load cells 50a-d is indicative of the location of the object on support deck 30. At step 170, controller 64 displays the location of the object on the same display as the patient's location was displayed in step 160, and controller 64 proceeds to re-start algorithm 150 by returning to step 154.

Figure 9:
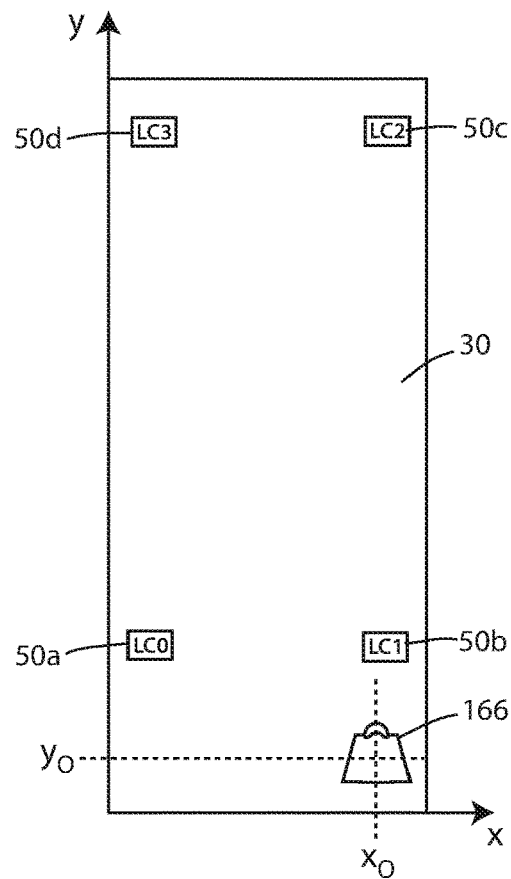
FIG. 9 is a plan view of the support surface of the person support apparatus of FIG. 1 illustrating an object positioned at a location $(x_o, y_o)$.
Figure 9A:
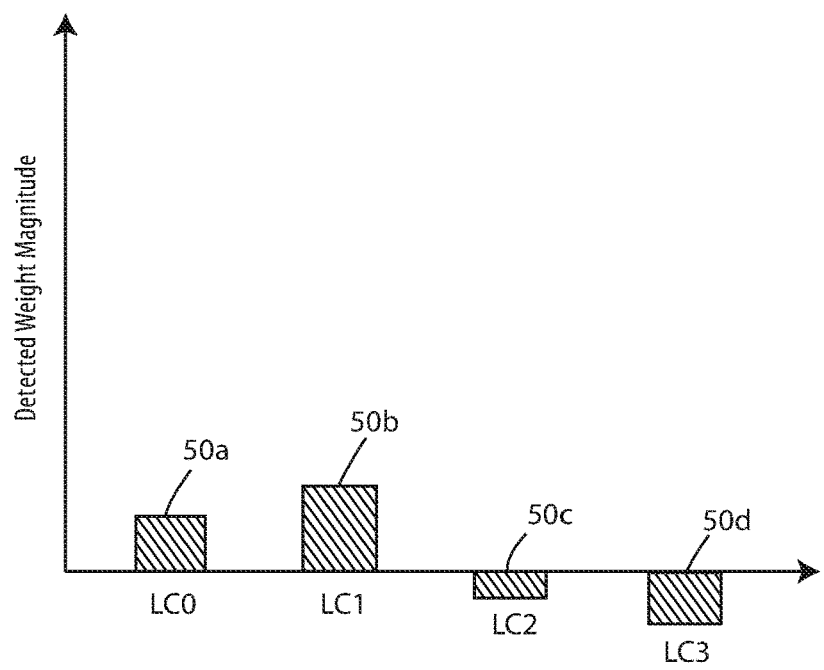
FIG. 9A is a graph illustrating the downward forces detected by the four load cells LC0, LC1, LC2, and LC3 when the object of FIG. 9 is positioned at location $(x_o, y_o)$.
Figure 10:
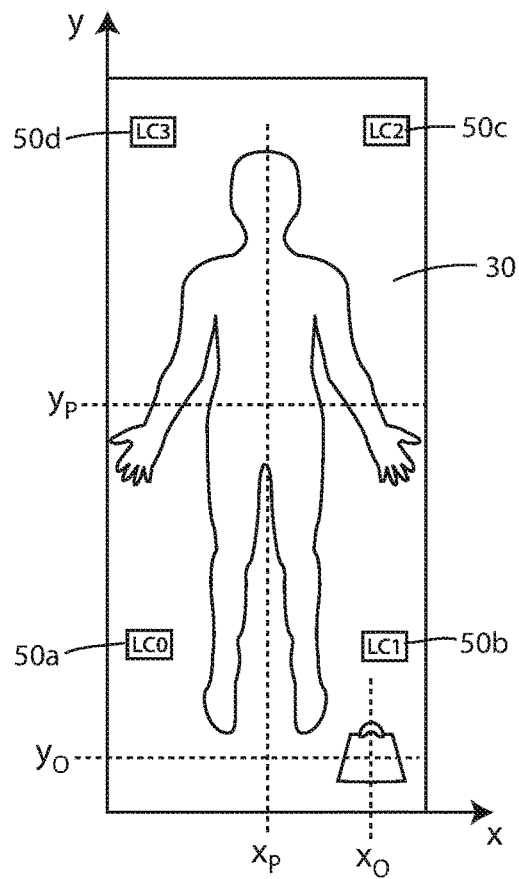
FIG. 10 is a plan view of the support surface of the person support apparatus of FIG. 1 illustrating both the occupant of FIG. 8 and the object of FIG. 9 positioned thereon at locations $(x_o, y_o)$ and $(x_p, y_p)$, respectively.

FIGS. 9-10 illustrate in greater detail one manner in which controller 64 carries out steps 164 and 168. FIGS. 9 and 9A illustrate an arbitrary placement and weight of object 166 when placed on support deck 30 at location $(x_o, y_o)$. More specifically, FIG. 9 illustrates object 166 placed at location $(x_o, y_o)$ while there is no occupant on support deck 30; and FIG. 9A illustrates the individual weights detected by each of the four load cells 50a-d when object 166 is placed on support deck 30 at location $(x_o, y_o)$.

Figure 10A:
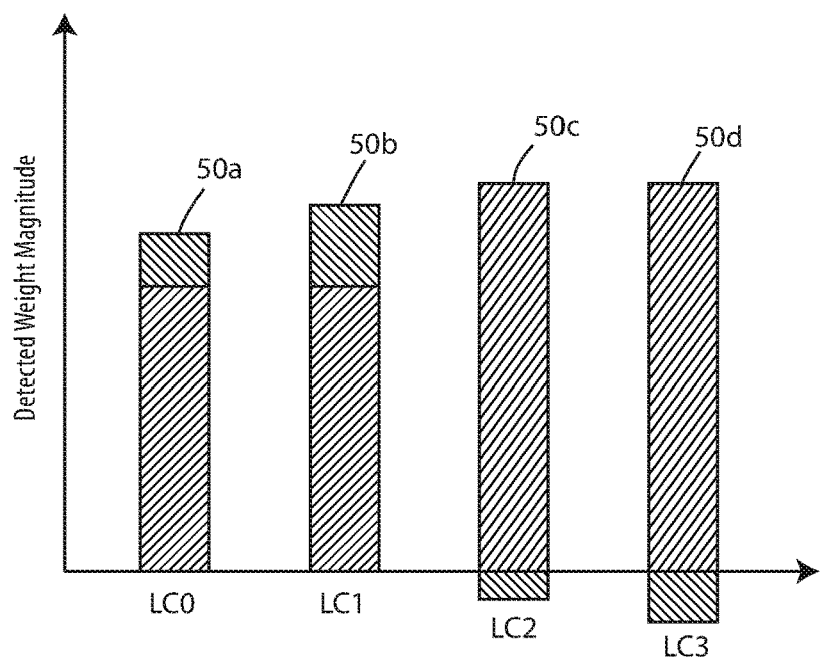
FIG. 10A is a graph illustrating the total downward forces detected by the four load cells LC0, LC1, LC2, and LC3 when the occupant and object of FIG. 9 are positioned at locations $(x_o, y_o)$ and $(x_p, y_p)$, respectively.
Figure 10B:
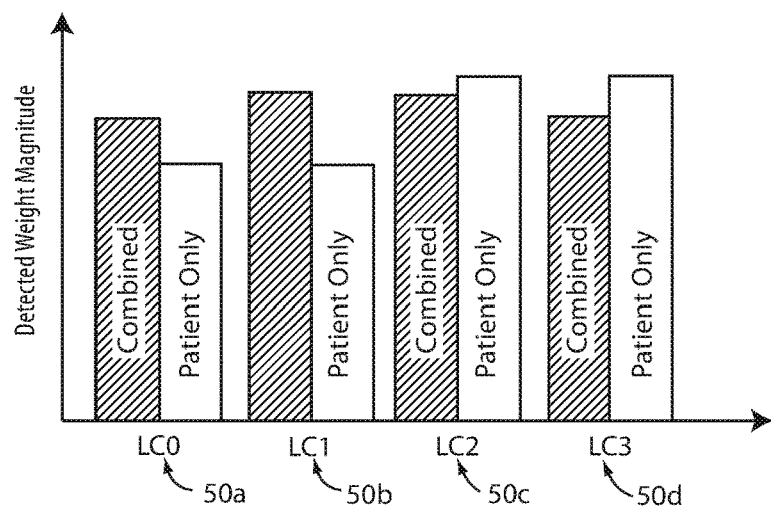
FIG. 10B is a graph of the total downward forces illustrated in FIG. 9A broken up into force components due to the occupant and force components due to the object.

FIGS. 10, 10A, and 10B illustrate the combination of both an occupant and object 166 on support deck 30. More specifically, FIG. 10 shows the occupant positioned at location $(x_p, y_p)$ and object 166 at location $(x_o, y_o)$. FIG. 10A illustrates the combined total weights sensed by each of the load cells 50a-d when both the occupant and object 166 are positioned on support deck 30 at the locations shown in FIG. 10. The portion of the weight sensed by each load cell 50 is shown divided according to which weight components are due to the occupant and which weight components are due to object 166. The weight due to object 166 is shaded with vertical stripes while the weight due to the occupant is shaded with diagonal stripes. FIG. 10B shows the weights due to the occupant separated from the total weights sensed by each of the load cells 50a-d.

Controller 64 is able to separately identify the location of object 166 from the location of the occupant by recording and utilizing a snapshot of the patient's weight distribution (e.g. FIG. 8A) at the moment object 166 is first added to support deck 30. Using the snapshot of the weight distribution of FIG. 8A, controller 64 presumes that the occupant has not moved at the moment object 166 is added, and therefore determines that any changes in the weight distribution shown in FIG. 8A after the object 166 has been added are indicative of the location of object 166, rather than indicative of occupant movement. Once the location of object 166 is known, any further changes in the distribution of the weights sensed by load cells 50a-d—but not the total cumulative weight sensed by load cells 50a-d—are interpreted by controller 64 as indicative of occupant movement, rather than movement of object 166. If the total cumulative weight sensed by load cells 50a-d changes (either up or down) after the location of object 166 has been determined, controller interprets such a change in total weight as either the addition of another object or the removal of object 166 (if the decrease in total cumulative weight matches the total weight of object 166). Controller 64 updates the display accordingly (i.e. by either displaying the location of the new object, or removing the image corresponding to object 166).

In at least one embodiment, controller 64 is further adapted to be able to track the location of multiple moving objects (including one or more occupants) on support deck. In such an embodiment, controller 64 gathers, records, and analyzes data regarding the movement characteristics of an occupant of support deck 30. Thereafter, if a moving object, such as child, therapy animal, or other moving animate object, is added, controller 64 uses the gathered statistical data regarding the occupant to distinguish between those changes in the weight distribution sensed by load cells 50a-d that are due to the occupant movement and those changes in the weight distribution sensed by load cells 50a-d that are due to the moving object. By distinguishing between the changes in the weight distribution due to the occupant's movement and the object's movement, controller 64 is able to determine the location of both the occupant and the object as they move.

In at least one embodiment, controller 64 is in communication with one or more image sensors, such as any of those disclosed in commonly assigned U.S. patent application Ser. No. 13/242,022 filed Sep. 23, 2011 by inventors Richard A. Derenne et al. and entitled VIDEO MONITORING SYSTEM, or U.S. patent application Ser. No. 61/989,243 filed May 6, 2014 by inventors Marko N. Kostic et al. and entitled PERSON SUPPORT APPARATUS WITH POSITION MONITORING, the complete disclosures of both of which are incorporated herein by reference. The image sensors provide data regarding the location of any animate or inanimate objects positioned on support deck 30. This data is combined and/or correlated with the data from load cells 50*a-d* and used by controller 64 to keep track of the location of one or more animate or inanimate objects on support deck 30. This image data provides both a cross-check to the load cell data, as well as data sufficient to distinguish between changes in the weight distribution due to the occupant's movement and changes due to the object's movement, particularly in situations where the statistical methods mentioned above may not be sufficient to reliably distinguish between the movement components.

In still another embodiment, controller 64 is itself configured to determine whether object 166 is an animate object or an inanimate object. Controller 64 determines that object 166 is inanimate if its location does not move for more than predetermined amount of time. Controller 64 concludes that object 166 is an animate object if it detects movement of object 166. Controller 64 may also be adapted, in at least one embodiment, to detect vibrations emanating from object 166 if object 166 is a mechanical device having a motor, such as a pump, ventilator, or the like. Controller 64 detects the repetitive vibrations from the object 166 and concludes that, in the absence of significant movement of the center of gravity of object 166, the vibrations are due to one or more motors in the device. Controller 64 records the location of object 166 and the time during which the object 166 was present on support deck 30 in a log that is retrievable by a user via control panel 52, or from a remote location that is in communication with person support apparatus 20 via communications link 88.

Figure 11:
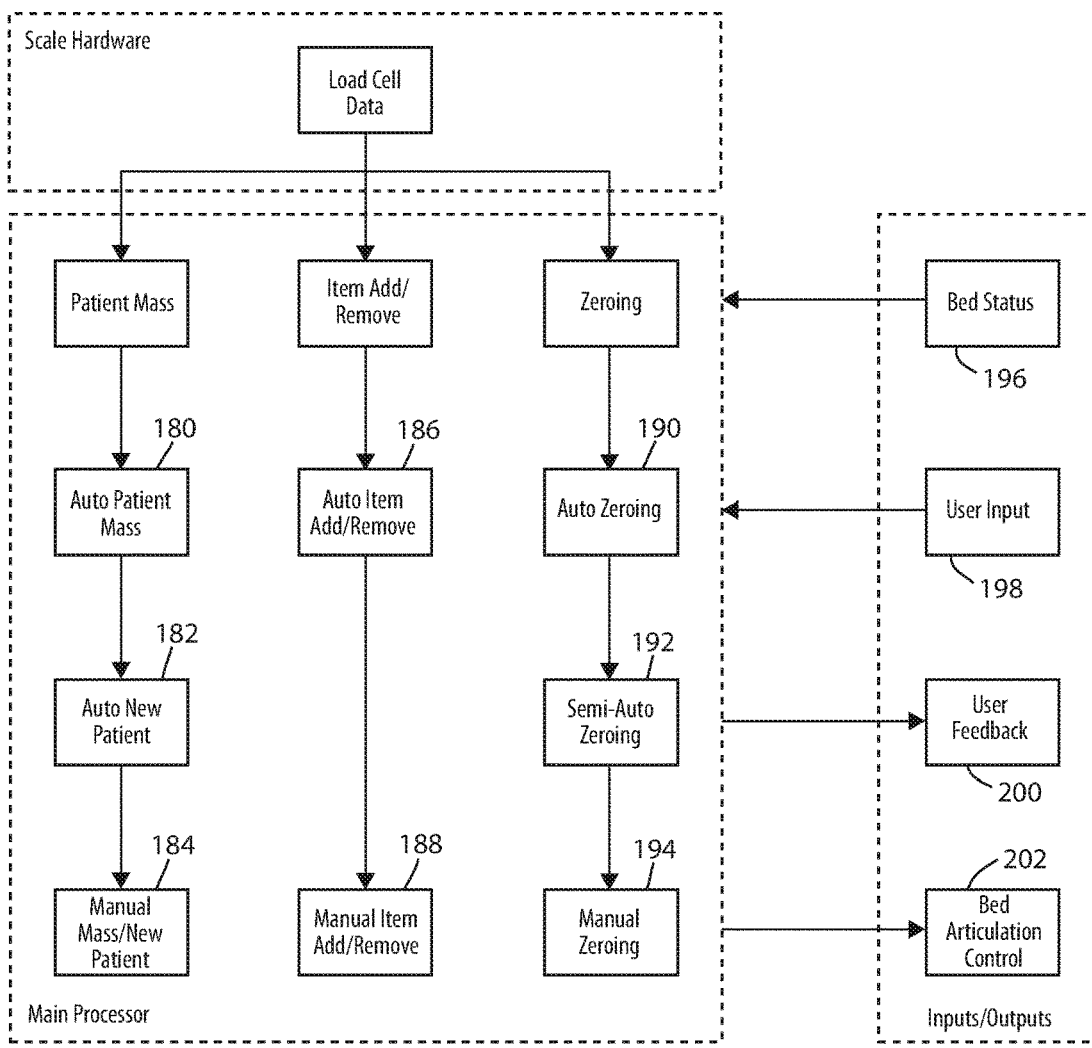
FIG. 11 is a diagram of several illustrative functions that may be implemented on the person support apparatus of FIG. 1, included functions relating to manual and automatic weighing, manual and automatic object detection, and manual and automatic zeroing of a scale system.

FIG. 11 is a diagram illustrating several additional functions that may be performed by controller 64 either alone or in combination with any of the aforementioned algorithms 90, 90*a*, 150, and/or any of the aforementioned variations of algorithms 90, 90*a*, and/or 150. More specifically, FIG. 11 illustrates an automatic weighing function 180, an automatic new patient detection function 182, a manual weighing and/or manual new patient function 184, an automatic object detection/removal function 186, a manual object detection/removal function 188, an automatic zeroing function 190, a semi-automatic zeroing function 192, and a manual zeroing function 194. Functions 180-194 are all performed by controller 64 in at least one embodiment. In other embodiments, controller 64 performs only a subset of these functions. In the embodiment shown in FIG. 11, all of the functions 180-194 are performed based upon data from the load cells 50*a-d*. It will be understood by those skilled in the art that functions 180-194 can be performed based upon weight data gathered by different types of sensors as well.

Controller 64 carries out automatic patient/occupant weighing function 180 by continuously monitoring the outputs of load cells 50*a-d* immediately, or nearly immediately, upon power-up of person support apparatus 20 such that any weight changes detected thereafter that are above a threshold are interpreted by controller 64 as due to the addition of an occupant/patient onto support deck 30. Details of various manners in which this function can be achieved are described in commonly assigned U.S. patent application Ser. No. 14/212,367 filed Mar. 14, 2014 by inventors Michael Joseph Hayes et al. and entitled PATIENT SUPPORT APPARATUS WITH PATIENT INFORMATION SENSORS, the complete disclosure of which has already been incorporated herein by reference.

In at least one embodiment, controller 64 carries out automatic occupant weighing function 180 by also examining the angular orientation of support deck 30 relative to horizontal, as well as the angular orientation of any of sections 36, 38, 40, and/or 42 with respect to deck 30. In one embodiment, controller 64 automatically moves support deck 30 and/or any of its sections 36-42 to a flat orientation prior to automatically determining the weight of the occupant. In another embodiment, controller 64 leaves deck 30 and/or its sections 36-42 in their current orientation, but applies any necessary correction factors to the readings from load cells 50*a-d* that take into account the angular orientations of deck 30 and/or its individual sections 36-42. In one embodiment, the corrections to the load cell readings due the tilting of deck 30 are carried out in the manner described in commonly assigned U.S. Pat. No. 7,702,481 entitled DIAGNOSTIC AND CONTROL SYSTEM FOR A PATIENT SUPPORT, the complete disclosure of which is hereby incorporated herein by reference.

Automatic occupant weighing function 180 allows a caregiver to determine a weight of the occupant of person support apparatus 20 without having to first zero load cells 50*a-d* and without having to manually press any buttons, or other controls, instructing controller 64 to take a weight reading. Once the patient/occupant's weight reading is taken by function 180, controller 64 displays this weight on display 56 and/or sends this weight reading to one or more remote electronic devices 82 (e.g. an electronic medical records server). Controller 64 also time stamps the weight reading and, if sent remotely, includes identification data in the weight message sent over communications link 88 that is sufficient to identify the occupant of person support apparatus 20 (such as an occupant ID number, or a person support apparatus ID number, or the like).

Controller 64 is also configured in at least one embodiment to automatically determine if a new occupant, such as a new patient, has entered onto support deck 30. In one embodiment, controller 64 performs this by comparing the current weight sensed by load cells 50*a-d* with a previously stored weight of the previous occupant. If the previously stored weight and the current weight are substantially the same, controller 64 concludes that the occupant is the same occupant as the previous occupant. If the current weight is not substantially the same as the previously stored weight, controller 64 concludes that a new occupant has entered onto support deck 30. Further details of one algorithm that may be used to perform function 182 are disclosed in the aforementioned U.S. application Ser. No. 14/212,367.

Manual weighing and/or manual new patient detection functions 184 are carried out in conventional manners. That is, manual weight and/or manual detection of a new occupant are carried out, in at least one embodiment, by one or more controls 54 on control panel 52 that a caregiver manipulates in order to weigh the occupant and/or to indicate to person support apparatus 20 that the occupant of person support apparatus 20 is a new occupant.

Function 186 of automatically detecting an object's addition or removal is carried out by controller 64 in any of the manners disclosed in the aforementioned U.S. application Ser. No. 14/212,367. Generally speaking, controller 64 carries out this function by detecting and recording changes in the total weight sensed by load cells 50*a-d*. Static additions of weight are determined to correspond to the addition of an object, while static reductions in the detected weight are determined to correspond to the removal of an object.

Manual object addition and/or removal function 188 is carried out by one or more controls 54 on control panel 52 that a user, such as a caregiver, manipulates in order to manually instruct controller 64 that an object has either been removed from support deck 30 or added to support deck 30.

Auto-zeroing function 190 is carried out by controller 64 in at least one embodiment by consulting a manufacturer's tare weight stored in memory 80. The manufacturer's tare weight is the weight that the manufacturer of person support apparatus 20 has determined is the normal expected tare weight sensed by load cells 50*a-d* when no external objects (e.g. mattress, bedding, occupant, etc.) are added to support deck 30. Controller 64 consults this value upon power-up of person support apparatus 20 and compares the currently sensed load cell readings with this value. If the current load cell readings are substantially the same as (or within a specified level of tolerance of) the manufacturer's stored tare value, then controller 64 concludes that no external weight is present on support deck 30 and that any differences between the current weight reading and the manufacturer's tare value are due to variations in the manufacture of an individual person support apparatus 20 and/or variations in individual load cells 50*a-d*. When no substantial variation exists, or the variation is within the pre-stored tolerance, between the current weight reading and the manufacturer's tare value, controller 64 sets the current weight reading as the new tare value and uses thereafter as the proper tare value for person support apparatus 20. If the variation between the current weight reading and the manufacturer's tare value exceeds the pre-stored tolerance, then controller 64 provides an indication on control panel 52 that an automatic zeroing of the load cells could not be accomplished.

In at least one embodiment, controller 64 carries out the automatic zeroing function 190 by, in addition to the steps described above, also automatically checking to see if support deck 30 and its sections 36-42 are all in a flat orientation prior to setting the current weight reading to the new tare reading. If deck 30 and/or its sections 36-42 are not all in the flat orientation (as determined from one or more suitable angle sensors that are in communication with controller 64), controller 64 provides an indication on control panel 52 indicating that the automatic zeroing process cannot be performed until deck 30 and its sections are moved to flat orientations. Alternatively, in at least one embodiment, controller 64 automatically moves deck section 30 and its sections 36-42 to flat orientations if they are not currently in flat orientations. Thereafter, controller 64 takes a weight reading from load cells 50*a-d* and carries out the automatic zeroing process described above. This step of checking the orientation of deck section 30 and its sections 36-42 prior to taking a weight reading is performed in order to account for inaccuracies in the load cell readings 50*a-d* that may be introduced, depending upon the design of person support apparatus 20, when deck 30 and/or its sections 36-42 are not in a flat orientation.

Semi-automatic zeroing function 192 is accomplished in the same manner as automatic zeroing function 190 described above but requires at least one manipulation of a control 54 by a user prior to carrying out the zeroing function. In at least one embodiment, control panel 52 includes a control 54 that, when activated, carries out the zeroing function without requiring any further manipulation of that control 54, or any other controls. For example, in one embodiment, a user presses a button on control panel 52 that thereafter causes controller 64 to carry out the steps described above for function 190. The user does not need to press any addition buttons, such as those that control the orientation of support deck 30 and/or its sections 36-42. Instead, controller 64 automatically flattens deck 30 and/or its sections in response to the pressing of the button that carries out the zeroing process. This eliminates the need to press multiple buttons, or manipulate multiple controls, in order to carry out the zeroing function.

Controller 64 is also configured to carry out manual zeroing function 194. This may be carried out in any conventional manner and requires a user to manually flatten deck 30 and/or its sections 36-42, as well as to manually instruct controller 64 when no load is present on support deck 30 so that controller 64 can take a weight reading at that time. Further, after the weight reading is taken, controller 64 presents the user with the results of that weight reading and requests, and waits for, approval from the user before using that weight reading as the new tare value.

In carrying out functions 180-194, controller 64 may receive and/or transmit one or more input and outputs, such as inputs/outputs 196-202 illustrated in FIG. 11. More specifically, status inputs 196 provide controller 64 with relevant information concerning the status of person support apparatus 20, such as, but not limited to, the angular orientation of deck 30 and/or its sections 36-42. User inputs 198 correspond to inputs that are made by a user using any of controls 54 on control panel 52, and/or any other controls on person support apparatus 20. User feedback 200 corresponds to information that is displayed on display 56 of control panel 52 (or elsewhere) that is relevant to any of functions 180-194. Bed articulation controls 202 correspond to commands sent out by controller 64 to automatically move one or more portions of person support apparatus 20, such as, but not limited to, support deck 30 and/or its sections 36-42.

In at least one embodiment, controller 64 is adapted to not only monitor the location of the occupant of support deck 30 and determine whether or not the occupant has rolled onto his or her side, but it is also adapted to determine whether an occupant has spun on support deck 30. Spinning refers to the occupant rotating onto his or her side from his or her back, or vice versa, without substantially changing his or her lateral position on support deck 30. Controller 64 is adapted to detect spinning by monitoring the lateral movement of the occupant's center of gravity and looking for lateral movement of the center of gravity toward one side of the support deck 30 followed by a return of the center of gravity to nearly the same position as prior to the spin. Such spinning movement is distinguished from rolling of the occupant onto his or her side by the fact that the lateral movement of an occupant during a spin is smaller than the lateral movement of an occupant during a roll. Controller 64 is further adapted to record in memory 80 that a spin (and/or a roll) has occurred, as well as the time of the spin (and/or roll). This information is stored in a log inside memory 80 that is retrievable by a user via control panel 52, or from a remote location that is in communication with person support apparatus 20 via communications link 88.

In at least one embodiment, controller 64 is also configured to record all movement of an occupant of person support apparatus 20 and record this movement in a log that is retrievable by a user via control panel 52, or from a remote location that is in communication with person support apparatus 20 via communication link 88. This log enables a user, such as a caregiver of a patient supported on person support apparatus, to retrieve information indicating how frequently the patient has moved, what kind of movement the patient has engaged in, and when the last movement was. This allows the caregiver to determine whether the patient needs additional movement in order to help prevent the formation of bed sores, or for other medical reasons. In one embodiment, controller 64 is adapted to issue an alert if the occupant does not engage in a minimum amount of movement for a specified time range. The amount of movement and time range are user-configurable in at least one embodiment.

It will be understood by those skilled in the art that the leaky bucket algorithm used with exit alert algorithm 90 can be applied to other fields besides person support apparatuses. Indeed, exit alert algorithm 90 can be applied to other fields where the movement of an individual outside of a specific area or zone is desirably monitored and an alert is issued prior to the person actually leaving the area or zone. One application in which exit alert algorithm 90 can be applied outside the field of person supports is playground monitoring of children. When so applied, controller 64 is in communication with a location monitoring device worn by a child, or otherwise positioned so as to continuously detect the location of the child. The kinetic energy of the child is continuously monitored and converted to an input into a motion parameter counter that "fills up" if the kinetic energy rises too quickly. The motion parameter counter is decremented at a steady rate in a manner similar to that described above with respect to algorithm 90. Any appropriate type of alert may be forwarded if the child's movement exceeds the threshold toward any of the boundaries of the play area. Still other applications of exit alert algorithm 90 and/or 90A are possible.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A person support apparatus comprising:
   a frame;
   a deck supported on the frame and adapted to support a person thereon;
   a plurality of force sensors coupled to the frame and adapted to detect a load supported by the frame;
   a display;
   a memory having stored therein an estimated tare weight value, the estimated tare weight value determined by a manufacturer of the person support apparatus; and
   a controller in communication with the plurality of force sensors, the controller configured to take a weight reading of the load using outputs from the force sensors, to automatically use the weight reading as an actual tare weight value only if the weight reading is within a threshold amount of the estimated tare weight value, to determine from the weight reading if an object is placed on the deck, to determine a location of the object, and to display the location of the object on the display.

2. The person support apparatus of claim 1 wherein the controller is further adapted to determine a weight of the object without requiring the object to be removed from the deck.

3. The person support apparatus of claim 2 wherein the controller is further adapted to determine if the object is an inanimate object or an animate object based on the outputs from the force sensors.

4. The person support apparatus of claim 3 wherein the controller is further adapted to automatically adjust the actual tare weight value by the weight of the object if the object is an inanimate object.

5. The person support apparatus of claim 3 wherein the controller is further adapted to automatically adjust the actual tare weight value by the weight of the object only if the object is an inanimate object and the location of the object corresponds to an expected location for the object.

6. The person support apparatus of claim 5 wherein the object includes at least one of a mattress or a pillow.

7. A person support apparatus comprising:
   a frame;
   a plurality of elevation adjustment mechanisms coupled to the frame and adapted to adjust a height of the frame and an orientation of the frame;
   a deck supported on the frame and adapted to support a person thereon, the deck including a head section and at least one other section, and the head section being pivotable between a horizontal orientation and a non-horizontal orientation;
   an angle sensor adapted to detect an orientation of the head section relative to horizontal;
   a scale system adapted to detect a weight of the deck and any object positioned thereon;
   a memory having stored therein an estimated tare weight value for the scale system, the estimated tare weight value determined by a manufacturer of the person support apparatus; and
   a controller in communication with the scale system and the memory, the controller adapted to automatically use, upon power up of the person support apparatus, an actual weight reading from the scale system as an actual tare weight value if both the actual weight reading is within a threshold amount of the estimated tare weight value, and the angle sensor indicates the head section is in the horizontal orientation.

8. The person support apparatus of claim 7 wherein the scale system includes a plurality of force sensors coupled between the frame and a load frame so as to support the load frame on the frame, the load frame being adapted to support the deck.

9. The person support apparatus of claim 8 wherein the controller is adapted to use the actual tare weight value when determining the weight of the person on the deck.

10. The person support apparatus of claim 8 wherein the controller is adapted to determine whether the object is an animate object or an inanimate object based upon any changes in a location of the object.

11. The person support apparatus of claim 7 wherein the controller is further adapted to use weight readings from the scale system to determine when a person is present on the deck, to determine when an object different from the person is added to the deck, and to determine a location of a center of gravity of the object in a coordinate frame of reference defined with respect to the person support apparatus.

12. The person support apparatus of claim 11 further comprising a display, and wherein the controller is further adapted to display the location of the center of gravity of the object on the display.

13. A person support apparatus comprising:
a frame;
a deck supported on the frame and adapted to support a person thereon;
a scale system adapted to detect a weight of the deck and any object positioned thereon;
a memory having stored therein an estimated tare weight value for the scale system, the estimated tare weight value determined by a manufacturer of the person support apparatus; and
a controller in communication with the scale system and the memory, the controller adapted to use an actual weight reading from the scale system as an actual tare weight value if the actual weight reading is within a threshold amount of the estimated tare weight value; the controller further adapted to use weight readings from the scale system to determine when a person is present on the deck, to determine when an object different from the person is added to the deck, to determine a location of a center of gravity of the object on the person support apparatus, and to determine a separate location of a center of gravity of the person on the person support apparatus.

14. The person support apparatus of claim 13 wherein the controller is adapted to determine the weight of the person on the deck by subtracting the actual tare weight value from a total weight reading taken when the person is on the deck.

15. The person support apparatus of claim 13 wherein the controller is adapted to automatically use the actual weight reading from the scale system as the actual tare weight value without requiring a user to manipulate a control on the person support apparatus instructing the scale system to take the actual weight reading.

16. The person support apparatus of claim 13 wherein the memory further includes a second estimated tare weight value, wherein the controller is adapted to use the actual weight reading from the scale system as the actual tare weight value if the actual weight reading is within the threshold amount of the second estimated tare weight value.

17. The person support apparatus of claim 16 wherein the second estimated tare weight value is based upon a weight of one or more of a mattress, pillow, bedding, or equipment.

18. The person support apparatus of claim 13 wherein the controller is adapted to determine whether the object is an animate object or an inanimate object based upon any changes in the location of the center of gravity of the object.

19. The person support apparatus of claim 18 wherein the controller is adapted to determine if a second object is placed on the deck subsequently to the object and to determine the weight of the second object without requiring the object to be removed from the deck.

20. The person support apparatus of claim 19 wherein the controller is adapted to automatically adjust the actual tare weight value by an amount substantially equal to the weight of the second object if the second object is an inanimate object.

21. The person support apparatus of claim 13 wherein the scale system includes a plurality of force sensors coupled between the frame and a load frame so as to support the load frame on the frame, the load frame being adapted to support the deck.

22. The person support apparatus of claim 13 further comprising a plurality of elevation adjustment mechanisms coupled to the frame and adapted to adjust a height of the frame and an orientation of the frame, and wherein the deck includes a head section pivotable between a flat orientation and a non-flat orientation, and the person support apparatus further includes an angle sensor adapted to detect an angle of a head section, and wherein the controller does not use the actual weight reading from the scale system as the actual tare weight value if the actual weight reading is taken when the head section is in the non-flat orientation.

23. A person support apparatus comprising:
a frame;
a deck supported on the frame and adapted to support a person thereon;
a scale system adapted to detect a weight of the deck and any object positioned thereon;
a display;
a memory having stored therein an estimated tare weight value for the scale system, the estimated tare weight value determined by a manufacturer of the person support apparatus; and
a controller in communication with the scale system and the memory, the controller adapted to use an actual weight reading from the scale system as an actual tare weight value if the actual weight reading is within a threshold amount of the estimated tare weight value; the controller further adapted to use weight readings from the scale system to determine when a person is present on the deck, to determine when an object different from the person is added to the deck, to determine a location of a center of gravity of the object on the person support apparatus, and to display the location of the center of gravity of the object on the display.

* * * * *